US012642662B2

(12) United States Patent
Rister et al.

(10) Patent No.: US 12,642,662 B2
(45) Date of Patent: *Jun. 2, 2026

(54) LATERALIZED DUAL-MOBILITY ASSEMBLY

(71) Applicant: Smith & Nephew, Inc., Memphis, TN (US)

(72) Inventors: David W. Rister, Nesbit, MS (US); Stephen J. Lee, Memphis, TN (US); Jeffrey Lee, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 329 days.

This patent is subject to a terminal disclaimer.

(21) Appl. No.: 18/434,905

(22) Filed: Feb. 7, 2024

(65) Prior Publication Data

US 2024/0173136 A1 May 30, 2024

Related U.S. Application Data

(63) Continuation of application No. 17/750,774, filed on May 23, 2022, now Pat. No. 11,925,562, which is a (Continued)

(51) Int. Cl.
A61F 2/34 (2006.01)
A61F 2/30 (2006.01)
(Continued)

(52) U.S. Cl.
CPC .................. A61F 2/34 (2013.01); A61F 2/32 (2013.01); A61F 2/36 (2013.01); A61F 2/4684 (2013.01);
(Continued)

(58) Field of Classification Search
CPC ........ A61F 2002/3208; A61F 2002/344; A61F 2002/345; A61F 2/32; A61F 2/34;
(Continued)

(56) References Cited

U.S. PATENT DOCUMENTS

2007/0179629 A1 8/2007 Murphy
2014/0303743 A1 10/2014 Choudhury et al.
(Continued)

FOREIGN PATENT DOCUMENTS

DE 4401815 A1 8/1994
FR 2903882 A1 1/2008
(Continued)

OTHER PUBLICATIONS

"Delata Primary System, Acetabular Cups, Surgical Technique", Retrieved from www.limacorporate.com, Jun. 22, 2015.
(Continued)

*Primary Examiner* — Javier G Blanco
(74) *Attorney, Agent, or Firm* — KDW Firm PLLC

(57) ABSTRACT

A modular acetabular cup assembly includes an acetabular cup, and a liner seated in the cup. The cup includes an end face, an apex opposite the end face, and a central axis extending between the apex and a center point of the end face. The liner includes an articular surface having a center of rotation which defines a pivot point of the acetabular cup assembly. In certain embodiments, the pivot point is laterally offset from the center point such that the end face is located between the pivot point and the apex.

9 Claims, 15 Drawing Sheets

Related U.S. Application Data continuation of application No. 17/149,068, filed on Jan. 14, 2021, now Pat. No. 11,369,475, which is a continuation of application No. 16/342,120, filed as application No. PCT/US2017/056917 on Oct. 17, 2017, now Pat. No. 11,013,604.

(60) Provisional application No. 62/409,064, filed on Oct. 17, 2016.

(51) Int. Cl.
| | |
|---|---|
| *A61F 2/32* | (2006.01) |
| *A61F 2/36* | (2006.01) |
| *A61F 2/46* | (2006.01) |

(52) U.S. Cl.
CPC .............. *A61F 2002/30332* (2013.01); *A61F 2002/30495* (2013.01); *A61F 2002/305* (2013.01); *A61F 2002/30614* (2013.01); *A61F 2002/30616* (2013.01); *A61F 2002/3069* (2013.01); *A61F 2002/30769* (2013.01); *A61F 2002/3208* (2013.01); *A61F 2002/3401* (2013.01); *A61F 2002/3403* (2013.01); *A61F 2002/3414* (2013.01); *A61F 2002/344* (2013.01); *A61F 2002/345* (2013.01)

(58) Field of Classification Search
CPC .......... A61F 2/4684; A61F 2002/30614; A61F 2002/30616
See application file for complete search history.

(56) References Cited

U.S. PATENT DOCUMENTS

| | | |
|---|---|---|
| 2015/0025647 A1 | 1/2015 | Zhang |
| 2018/0028322 A1 | 2/2018 | Sharkey et al. |

FOREIGN PATENT DOCUMENTS

| | | |
|---|---|---|
| FR | 2904930 A1 | 2/2008 |
| FR | 2951071 A1 | 4/2011 |
| WO | 2004069091 A2 | 8/2004 |
| WO | 2004069091 A3 | 8/2004 |
| WO | 2007108848 A1 | 9/2007 |
| WO | 14052768 A2 | 4/2014 |

OTHER PUBLICATIONS

International Search Report; European Patent Office; International Application No. PCT/US2017/056917; Feb. 12, 2018; 5 pages.
Written Opinion of the International Searching Authority; European Patent Office; International Application No. PCT/US2017/056917; Feb. 12, 2018; 6 pages.
Communication pursuant to Article 94(3) EPC for EP Application No. 17794140.8, dated Dec. 14, 2020, original and translated document, 5 pages.
Office Action for Chinese Patent Application No. 201780062102.8, dated Feb. 8, 2021, original and translated documents, 13 pages.
European Patent Office, Extended European Search Report, dated Jun. 21, 2024; 8 pages.

430

LATERALIZED DUAL-MOBILITY ASSEMBLY

CROSS-REFERENCE TO RELATED APPLICATION

This application is a continuation of pending U.S. patent application Ser. No. 17/750,774, filed May 23, 2022, entitled "Lateralized Dual-Mobility Assembly", which is a continuation of U.S. patent application Ser. No. 17/149,068, filed Jan. 14, 2021, now U.S. Pat. No. 11,369,475, entitled "Lateralized Dual-Mobility Assembly", which is a continuation of U.S. patent application Ser. No. 16/342,120, filed Apr. 15, 2019, now U.S. Pat. No. 11,013,604, entitled "Lateralized Dual-Mobility Assembly", which application is a U.S. National Phase of International PCT Application No. PCT/US2017/056917, filed on Oct. 17, 2017, which claims the benefit of U.S. Provisional Patent Application No. 62/409,064, filed on Oct. 17, 2016, the contents of each application hereby incorporated herein by reference in their entirety.

TECHNICAL FIELD

The present disclosure generally relates to acetabular cup liners having lateralized pivot points, and more particularly but not exclusively relates to dual-mobility assemblies including such acetabular cup liners.

BACKGROUND

In certain total hip arthroplasty (THA) conditions, joint stability may be improved by increasing the tension provided to the soft tissue associated with the joint. Modern modular dual-mobility hip systems have shown promise in reducing the rate of dislocation by introducing increased femoral head size as compared to traditional THA systems, but are limited as compared to traditional THA in the modular options to address the degree of tension in the joint. In certain existing modular dual-mobility systems, an inner head component is mounted to the femoral component, and an outer head component is pivotally mounted to the inner head component to provide a dual-mobility femoral head assembly. Head length options in these dual-mobility constructs are limited by geometry, consequently limiting the soft tissue tensioning options available as compared to traditional total hip constructs.

In certain conventional dual-mobility assemblies of the species described above, skirted femoral heads are utilized to extend the mating cones and consequently increase soft tissue tension. However, head length options for modular femoral heads have been limited due to an increased risk of intraprosthetic disassociation between skirted femoral heads and the mobile bearing insert, as well as suboptimal wear characteristics.

Although dual-mobility bearings have been shown to reduce the rate of dislocation, there remains a desire to further reduce the risk of such dislocation. For these reasons among others, there remains a need for further improvements in this technological field.

SUMMARY

A modular acetabular cup assembly includes an acetabular cup and a liner seated in the cup. The cup includes an end face, an apex opposite the end face, and a central axis extending between the apex and a center point of the end face. The liner includes an articular surface having a center of rotation which defines a pivot point of the acetabular cup assembly. In certain embodiments, the pivot point is laterally offset from the center point such that the end face is located between the pivot point and the apex.

DETAILED DESCRIPTION OF ILLUSTRATIVE EMBODIMENTS

Figure 1:
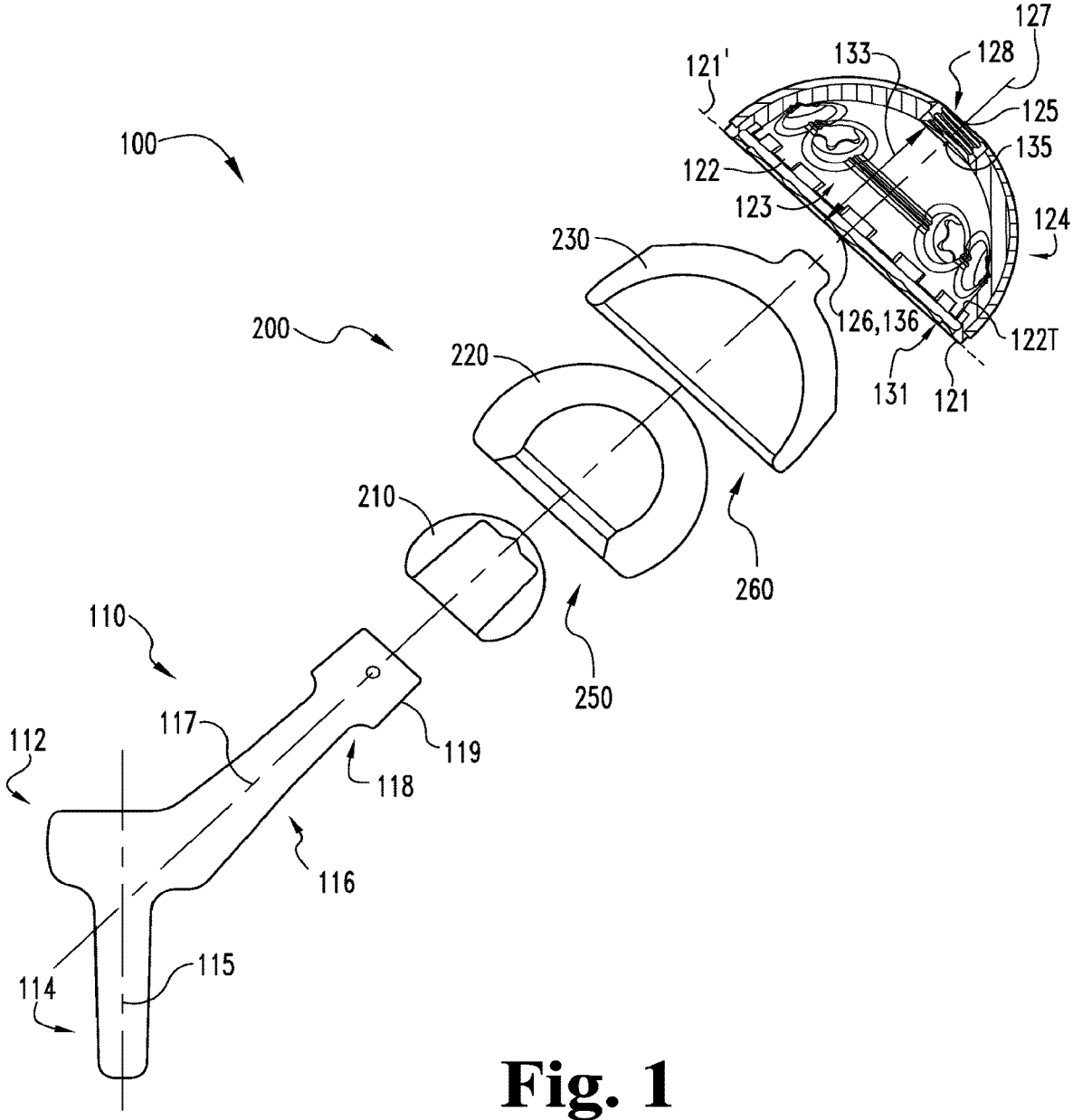
FIG. 1 is an exploded cross-sectional view of a total hip arthroplasty system including a dual-mobility assembly according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

As used herein, the term "mediolateral" is used to describe motion or spacing along a first axis, and the term "transverse" is used to denote motion or spacing along a transversely-extending second axis perpendicular to the first axis. In the coordinate system illustrated in FIG. 2, for example, the first or mediolateral axis is depicted as the vertical Y-axis, and the second or transverse axis is depicted as the horizontal X-axis. Additionally, the mediolateral Y-axis defines a medial direction (Y⁺) and an opposite lateral direction (Y⁻), which are respectively illustrated in FIG. 2 as an upward direction (Y⁺) and a downward direction (Y⁻), and which may be described herein with reference to such an orientation. These terms are used for ease and convenience of description, and need not reflect the orientation of the system with respect to the environment. Furthermore, motion or spacing along a direction defined by one of the axes need not preclude motion or spacing along a direction defined by another of the axes. For example, elements which are described as being transversely offset (i.e., offset along the transverse X-axis) from one another may also be offset from one another in a mediolateral direction, or may be mediolaterally aligned with one another. The terms are therefore not to be construed as limiting the scope of the subject matter described herein.

Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

Figure 2:
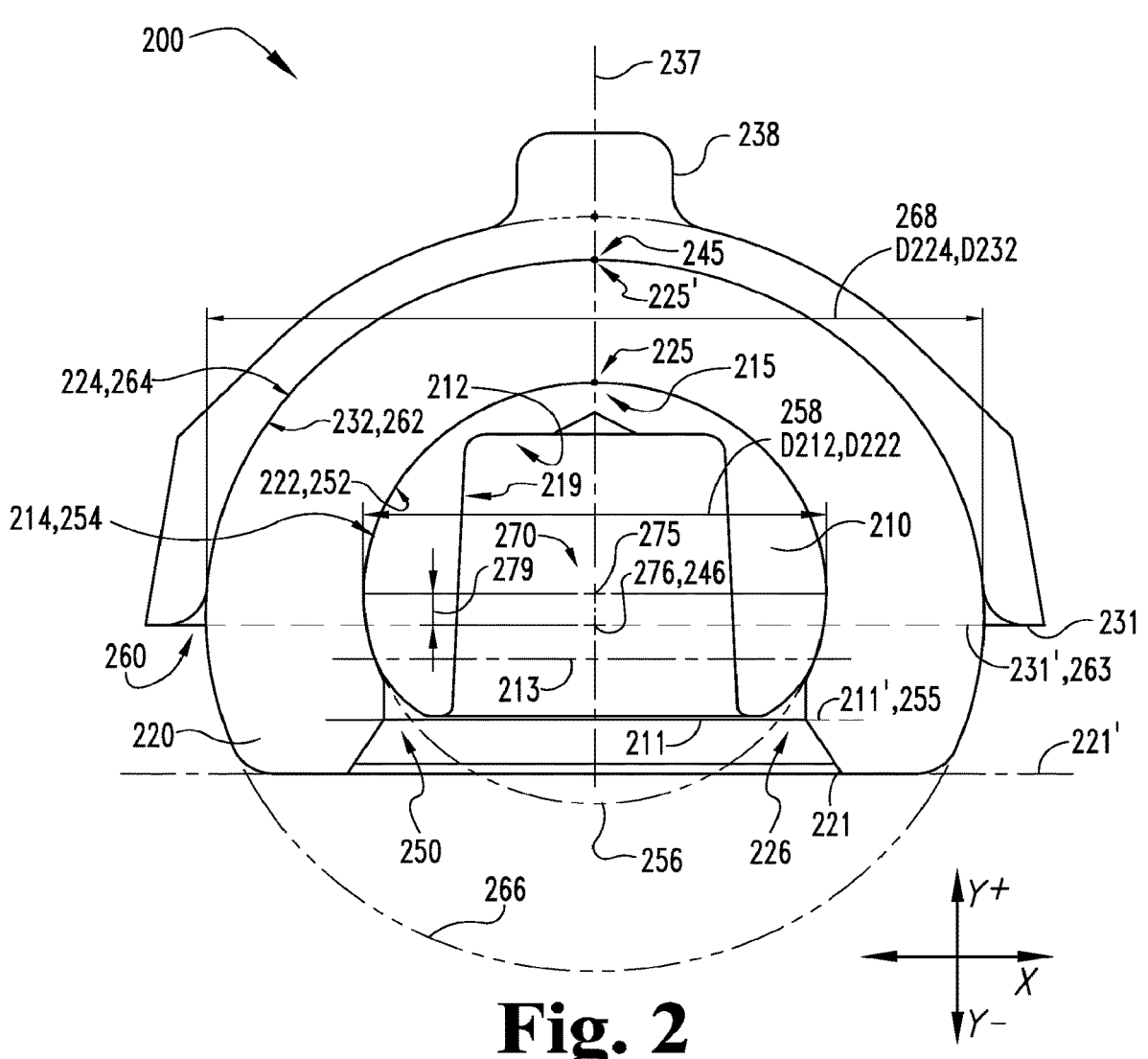
FIG. 2 is a cross-sectional view of the dual-mobility assembly illustrated in FIG. 1.

With reference to FIGS. 1 and 2, illustrated therein is a total hip arthroplasty system 100 according to certain embodiments. The system 100 is configured for use in a total hip arthroplasty procedure, and generally includes a femoral component 110 configured for implantation in a femur, an acetabular cup 120 configured for implantation in a hip, and a dual-mobility assembly 200 according to certain embodiments. The dual-mobility assembly 200 is mounted between the femoral component 110 and the acetabular cup 120, and defines a dual pivot 270 about which the femoral component 110 pivots relative to the acetabular cup 120. As described in further detail below, the dual pivot 270 includes a first pivot point 275 and a second pivot point 276, and an offset distance 279 is defined between the first and second pivot points 275, 276. In the illustrated embodiment, the pivot points 275, 276 are offset from one another such that the offset distance 279 has a non-trivial, non-zero value. In other embodiments, the pivot points 275, 276 may be coincident with one another such that the offset distance 279 is zero, or may be substantially coincident with one another such that the offset distance 279 has a trivial non-zero value.

With additional reference to FIG. 2, the dual-mobility assembly 200 generally includes a head 210 mounted to the femoral component 110, a liner 230 mounted in the acetabular cup 120, and an insert 220 mounted between the head 210 and the liner 230. The dual-mobility assembly 200 provides the system 100 with a first articular interface 250 and a second articular interface 260, each of which enables the femoral component 110 to pivot relative to the cup 120 about the dual pivot 270. More specifically, the first articular interface 250 is defined between the head 210 and the insert 220, and facilitates relative pivotal movement of the head 210 and insert 220 about the first pivot point 275. Similarly, the second articular interface 260 is defined between the insert 220 and the liner 230, and facilitates relative pivotal movement of the insert 220 and liner 230 about the second pivot point 276.

The components of the illustrated dual-mobility assembly 200 are modular, which may facilitate assembly of the dual-mobility assembly 200 in each of a plurality of configurations by selecting one or more of the components from a family of similar components. Each component family provides at least one variable characteristic tor the corresponding component such that the dual-mobility assembly 200 enables at least one characteristic of the system 100 to be adjusted. As described in further detail below, the illustrated dual-mobility assembly 200 provides the system 100 with an adjustable position for the dual pivot 270. More specifically, the assembly 200 enables the second pivot point 276 to be moved in at least one of a mediolateral direction and a transverse direction, thereby enabling a surgeon to adjust the tension in the soft tissue associated with the hip joint in which the system 100 is implanted.

The femoral component 110 includes a body 112, a stem 114 extending distally from the body 112 along a stem axis 115, and a neck 116 that extends from the body 112 along a neck axis 117 to a tapered end portion 118. The stem 114 is configured to be inserted into the medullary canal of a prepared femur, and may be porous to encourage bone ingrowth. The neck axis 117 is angularly offset from the stem axis 115 by an angle corresponding to the angle defined between the neck and shaft of a healthy femur. The tapered end portion 118 includes a tapered sidewall 119 that defines a taper angle relative to the neck axis 117, and which provides the tapered end portion 118 with a substantially frustoconical geometry.

The example cup 120 is generally hemispherical and includes a cup end face 121 extending along a cup end face plane 121', a cup inner surface 122 defining a cup cavity 123, and a cup outer surface 124. The end face 121 has a center point 126 and defines an end face opening 131 having a center point 136, which in the illustrated form is coincident with the center point 126 of the end face 121. The center points 126, 136 may alternatively be referred to herein as the cup face center point 126 and the cup opening center point 136. As described herein, the cup face center point 126 may serve as a point of reference in describing the position of one or more features relative to the cup 120. Accordingly, the cup face center point 126 may alternatively be referred to herein as the reference point 126.

The end face opening 131 is connected to the cavity 123, which is sized and configured to receive the liner 230. The outer surface 124 is configured to interface with a prepared acetabulum, and may be porous to encourage bone ingrowth. The cup 120 has an outer apex 125, an inner apex 135, and a central axis 127. In the illustrated form, the central axis 127 extends from the outer apex 125 to the center point 126 of the end face 121, and includes the inner apex 135. The illustrated cup 120 also includes an apex opening 128, which is formal at the outer apex 125 and extends along the central axis 127. Additionally, the cavity 123 has a depth dimension 133, which extends along the central axis 127 from the inner apex 135 to the center point 136 of the end face opening 131. Further details regarding the cup 120 are provided below with reference to FIG. 12.

The head 210 includes a head end face 211 extending along a head end face plane 211', an inner engagement surface 212, and an outer articular surface 214. The inner surface 212 defines a head cavity 213 sized and configured to receive the tapered end portion 118 of the neck 116. The head cavity 213 is defined in part by a tapered wall 219, which engages the tapered sidewall 119 to secure the head 210 to the femoral component 110. In certain embodiments the head 210 may be formed of a ceramic material. In other embodiments, the head 210 may be formed of a metallic material, such as oxidized zirconium, diffusion-hardened oxidized zirconium, or a cobalt-chromium alloy.

The insert 220 includes an insert end face 221 extending along an insert end face plane 221', an inner articular surface 222, and an outer articular surface 224. The inner surface 222 has an inner apex 225, and the outer surface 224 has an outer apex 225'. The inner surface 222 forms an insert cavity 223 sized and configured to receive the head 210. The insert 220 may further include a tapered inlet 226 connected to the end face 221 to facilitate insertion of the head 210 into the cavity 223. When the system 100 is assembled, the tapered inlet 226 may also provide a bearing surface that engages the neck 116 as the femoral component 110 pivots, thereby causing the insert 220 to pivot within the liner 230. The insert 220 may, for example, be formed of a polymeric material, such as standard polyethylene, cross-linked polyethylene, or ultra-high-molecular-weight polyethylene (UHMWPE).

Figure 3:
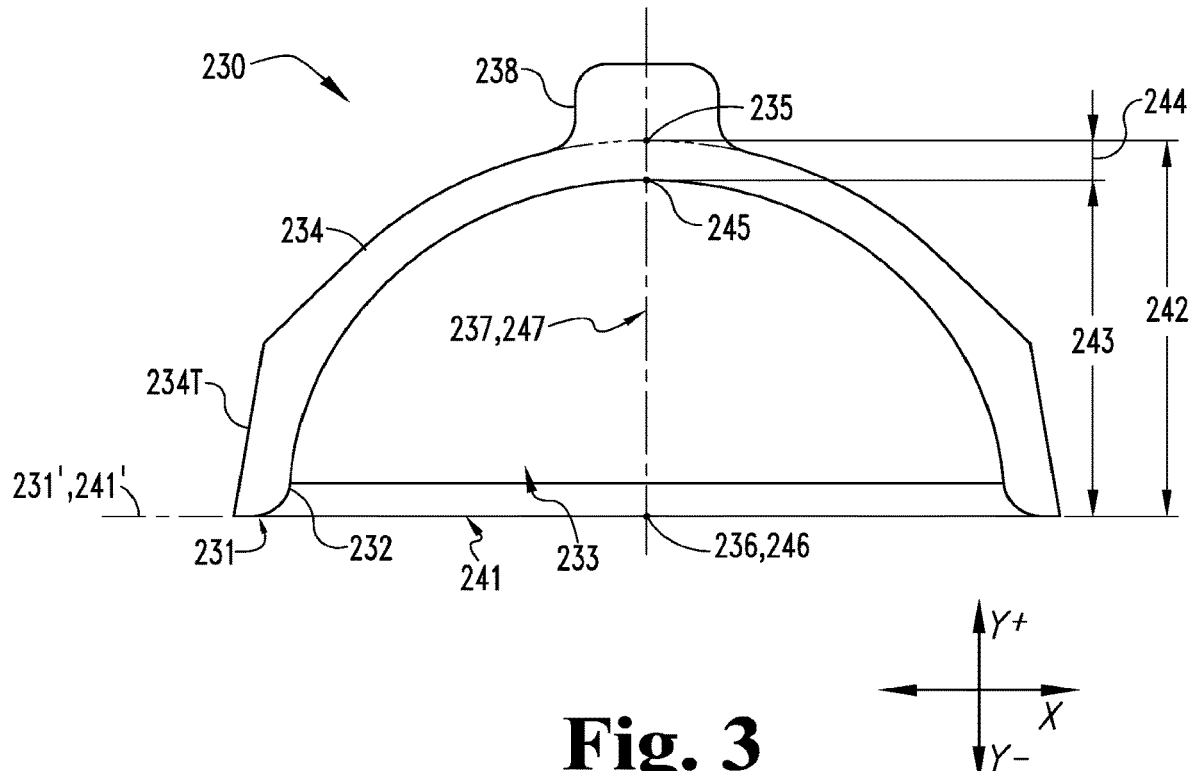
FIG. 3 is a cross-sectional view of a liner which may be utilized in connection with the dual-mobility assembly illustrated in FIG. 1.

With additional reference to FIG. 3, the liner 230 is generally hemispherical and includes a liner end face 231 extending along a liner end face plane 231', an inner articular surface 232 defining a liner cavity 233, and an outer surface 234. The end face 231 has a center point 236, and defines an end face opening 241 having a center point 246. The center points 236, 246 may alternatively be referred to herein as the liner face center point 236 and the liner opening center point 246. The end face opening 241 is connected to the cavity 233, which is sized and configured to receive the insert 220. The liner 230 has an outer apex 235 and an inner apex 245. The inner apex 245 may alternatively be considered to be the apex of the inner surface 232 and/or the apex of the liner cavity 233. The liner 230 may, for example, be formed of a metallic material, such as diffusion-hardened oxidized zirconium or a cobalt-chromium alloy.

The liner 230 has a geometric axis 237 which extends from the outer apex 235 to the center point 236 of the liner end face 231. The outer surface 234 includes a protrusion 238 that extends from the outer apex 235 along the geometric axis 237. The outer surface 234 may include a tapered wall 234T that engages a corresponding tapered wall 122T of the cup inner surface 122. When the liner 230 is received in the cup 120, the geometric axis 237 is aligned with the cup central axis 127, and the protrusion 238 extends into the apex opening 128. The outer surface 234 is configured to engage the cup inner surface 122 to releasably or fixedly secure the liner 230 to the cup 120. For example, the surfaces 122, 234 may include mating features that selectively retain the liner 230 within the cavity 123 of the cup 120. Additionally, the mating features may enable the liner 230 to be installed in the cup 120 in each of a plurality of rotational orientations relative to the cup axis 127. Certain non-limiting examples of such mating features are described in U.S. Pat. No. 9,463,094 to Allen at al., the contents of which are hereby incorporated by reference in their entirety.

When seated in the liner 230, the insert 220 is pivotable about the second pivot point 276 with three rotational degrees of freedom. In other words, the insert 220 is rotatable about each of three mutually orthogonal axes that intersect at the center point 246 of the end face opening 241. In the interest of ease and convenience of description, two of the rotational axes may be considered to be defined along the plane 241' of the end face opening 241, and the third rotational axis 247 may be considered to extend from the center point 246 to the inner apex 245. In the illustrated embodiment, the liner cavity 233 is centered at the geometric axis 237 of the liner 230. As a result, the center points 236, 246 are coincident with one another, the inner apex 245 is located on the geometric axis 237, and the rotational axis 247 is coincident with the geometric axis 237. As described in further detail below, however, it is also contemplated that the rotational axis 247 may be offset from the geometric axis 237.

The liner 230 has an effective height 242, a cavity height 243, and an apex thickness 244, each of which is measured in a mediolateral direction perpendicular to the end face 231 (i.e., in the vertical direction of FIG. 3). More specifically, the cavity height 243 is the distance by which the inner apex 245 is medially offset from the end face 231, the thickness 244 is the distance by which the outer apex 235 is medially offset from the inner apex 245, and the effective height 242 includes the cavity height 243 and the thickness 244. The effective height 242 corresponds to the height of the liner 230 relative to the cup inner apex 135 when the liner 230 is fully seated in the cup 120. As noted above, when the liner 230 is sealed in the cup 120, the protrusion 238 is received in the apex opening 128. Accordingly, the height of the protrusion 238 need not be included when considering the effective height 242 of the liner 230.

With specific reference to FIG. 2, the first articular interface 250 includes a first outer surface 252 formed by the insert 220, and a first inner surface 254 formed by the head 210. More specifically, the outer surface 252 is defined by the inner articular surface 222 of the insert 220, and the inner surface 254 is defined by the outer articular surface 214 or the head 210. Each of the outer surface 252 and the inner surface 254 corresponds to a respective cap of a first sphere 256, which has a first diameter 258 and centered at the first pivot point 275. As used herein, a cap of a sphere or a spherical cap is the region of the sphere which lies on one side of a given plane that intersects the sphere. For example, the outer surface 252 corresponds to the portion of the sphere 256 above a plane 253, and the inner surface 254 corresponds to the portion of the sphere 256 above a plane 255. Thus, each of the surfaces 252, 254 may be considered to be spherical about the first pivot point 275. As used herein, the term "spherical" is used to describe a geometry that is defined by at least a portion of a sphere, and does not necessarily require that the described feature define a full sphere. Those skilled in the art will readily appreciate that where a plane intersects a sphere to define a spherical cap, a line extending orthogonal to the plane and through the center of the sphere intersects an apex of the cap.

As will be appreciated, the nominal diameter D222 of the insert inner surface 222 may be slightly greater than the nominal diameter D214 of the head outer surface 214. Such a feature may, for example, ensure that the head 210 and insert 220 remain pivotable relative to one another while allowing for variations of the diameters D214, D222 within manufacturing tolerances. In such a case, each of the surfaces 252, 254 may nonetheless be considered to correspond to a cap of the sphere 256, and each of the diameters D214, D222 may nonetheless be considered to correspond to the diameter 258 of the sphere 256.

The second articular interface 260 includes a second outer surface 262 formed by the liner 230 and a second inner surface 264 formed by the insert 220. More specifically, the outer surface 262 is defined by the inner articular surface 232 of the liner 230, and the inner surface 264 is defined by the outer articular surface 224 of the insert 220. Each of the outer surface 262 and the inner surface 264 corresponds to a respective cap of a second sphere 266, which has a second diameter 268 and is centered at the second pivot point 276. For example, the outer surface 262 corresponds to the portion of the sphere 266 above a plane 263, and the inner surface 264 corresponds to the portion of the sphere 266 above a plane 265. In the illustrated form, the plane 263 is defined at the end face 231 of the liner 230, and intersects the second pivot point 276. As a result, the spherical cap to which the outer surface 262 corresponds is a hemisphere. It is also contemplated that the outer surface 262 may correspond to another form of spherical cap, for example in embodiments in which the plane 263 does not intersect the pivot point 276.

As should be appreciated, the nominal diameter D232 of the liner inner surface 232 may be slightly greater than the nominal diameter D224 of the insert outer surface 224 so as, for example, to ensure that the insert 220 remains pivotable relative to the liner 230 while allowing for variations of the diameters D224, D232 within manufacturing tolerances. In such a case, each of the surfaces 262, 264 may nonetheless be considered to correspond to a spherical cap defined by the second sphere 266, and each of the diameters D224, D242 may nonetheless be considered to correspond to the diameter 268 of the sphere 266.

In certain embodiments, the first and second pivot points 273, 276 may be coincident with one another such that the dual pivot 270 is provided as a single pivot point. However, in the illustrated embodiment, the second pivot point 276 is located on the end face plane 231' of the liner 230, and the first pivot point 275 is slightly medialized relative to the second pivot point 276. In other words, the first pivot point 275 is slightly offset from the second pivot point 276 in the medial direction. As a result, the rotational orientation of the dual pivot 270 may change as the femoral component 110 pivots through its range of motion. More specifically, rotation of the liner 230 about the second pivot point 276 may cause the first pivot point 275 to move relative to the second pivot point 276. In contrast, the second pivot point 276 maintains a fixed location relative to the liner 230 mounted in the cup 120, and may therefore be considered to define the position of the dual pivot 270. In other words, a description of the location of one of the dual pivot 270 and the second pivot point 276 may equivalently be understood as describing the location of the other of the dual pivot 270 and the second pivot point 276.

FIG. 2 illustrates the dual-mobility assembly 200 in a home position, in which the insert inner apex 225 is aligned with the head apex 215, and the insert outer apex 225' is aligned with the liner inner apex 245. With the dual-mobility assembly 200 in the home position and mounted to the cup 120, the liner outer apex 235 is also aligned with the cup inner apex 135. Unless indicated otherwise, a description of a position or dimension may be assumed to describe the position or dimension when the dual-mobility assembly 200 is in the home position and is mounted to the cup 120. For example, a description of the head end face plane 211' as being laterally offset from the liner end face plane 231' is to be understood as referring to the relative positions with the assembly 200 in the home position. Those skilled in the art will readily recognize that when the assembly 200 is not in the home position, the end face planes 211', 231' may intersect one another.

With the system 100 assembled, the two articular interfaces 250, 260 provided by the dual-mobility assembly 200 facilitate pivoting of the femoral component 110 about the dual pivot 270 in two manners. More specifically, the first articular interface 250 facilitates pivoting of the head 210 relative to the insert 220 about the first pivot point 275, and the second articular interface 260 facilitates pivoting of the insert 220 relative to the liner 230 about the second pivot point 276. As described in further detail below, the modularity of the dual-mobility assembly 200 enables certain characteristics of the system 100 to be adjusted while maintaining the same femoral component 110 and acetabular cup 120.

Figure 4:
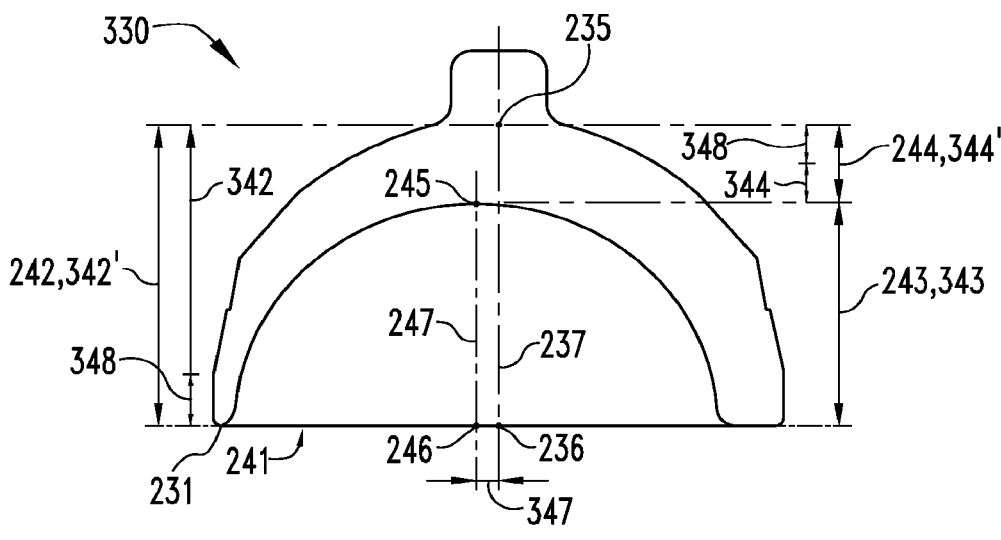
FIG. 4 is a cross-sectional view of one embodiment of a liner family which includes first, second, and third liner species.

With additional reference to FIG. 4, illustrated therein is a liner family 300 including a plurality of liner species 310, 320, 330. In certain embodiments, the liner family 300 may be provided in a kit for the dual-mobility assembly 200, such as the kit 700 described below with reference to FIG. 8. In other embodiments, a liner family may be provided as a standalone kit configured for use with a cup 120 and insert 220 having predetermined configurations. Each of the liner species 310, 320, 330 may be selected as the liner 230 of the dual-mobility assembly 200, and includes the features described above with reference to the liner 230. In the interest of conciseness, the following description focuses primarily on features of the liner species 310, 320, 330 that are different from those described above with reference to the liner 230.

In the illustrated form, the liner family 300 includes a first liner species 310, a second liner species 320, and a third liner species 330, each of which is configured to be seated in the cup 120 and to receive the insert 220. The liner species 310, 320, 330 are substantially similar to one another, and differ primarily in certain dimensions thereof. For example, while the cavity height 243 of each of the liner species 310, 320, 330 defines a substantially identical liner cavity height 343, the apex thickness 244 of the first liner species 310 is a first apex thickness 344, and the apex thickness 244 of the second and third liner species 320, 330 is a second apex thickness 344' different from the first apex thickness 344. More specifically, the second apex thickness 344' is greater than the first apex thickness 344 by a lateral offset distance 348. As a result, the effective height 242 of the first liner species 310 is a first effective height 342, and the effective height 242 of each of the second and third liner species 320, 330 is a second effective height 342' greater than the first effective height 342 by the lateral offset distance 348. The first liner species 310 may be considered to have a lateral offset distance of zero.

In certain embodiments, the first effective height 342 may correspond to the depth dimension 133 of the cup cavity 123, and the second effective height 342' may be greater than the depth dimension 133 by a predetermined distance. Additionally, while the second and third liner species 320, 330 have the same effective height 342', the third liner species 330 also includes a non-zero transverse offset distance 347 between the geometric axis 237 and rotational axis 247 thereof. In certain embodiments, the geometric and rotational axes 237, 247 of the first and second liner species 310, 320 may be considered to have a transverse offset distance of zero.

With additional reference to FIGS. 5-7 and FIGS. 13-18, the modular nature of the dual-mobility assembly 200 facilitates utilization of the assembly 200 in each of a plurality of different configurations 201, 202, 203 within the system 100. In the interest of clarity, certain components of the system 100, such as the femoral component 110 and the head 210, have been omitted from FIGS. 5-7, but are illustrated in FIGS. 13-18.

Figure 5:
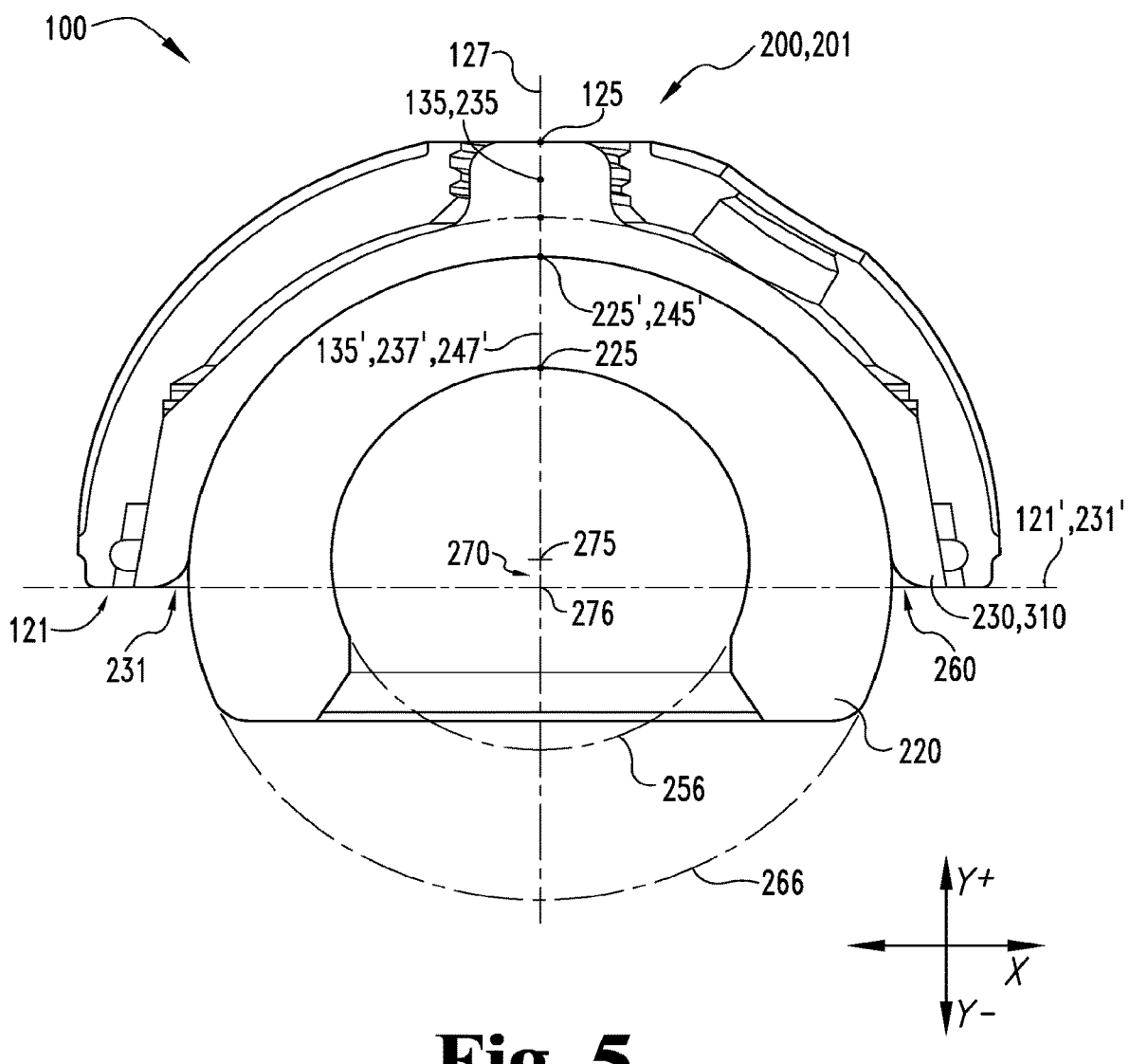
FIG. 5 is a cross-sectional view of a first configuration of the dual-mobility assembly which includes the first liner species illustrated in FIG. 4.
Figure 14:
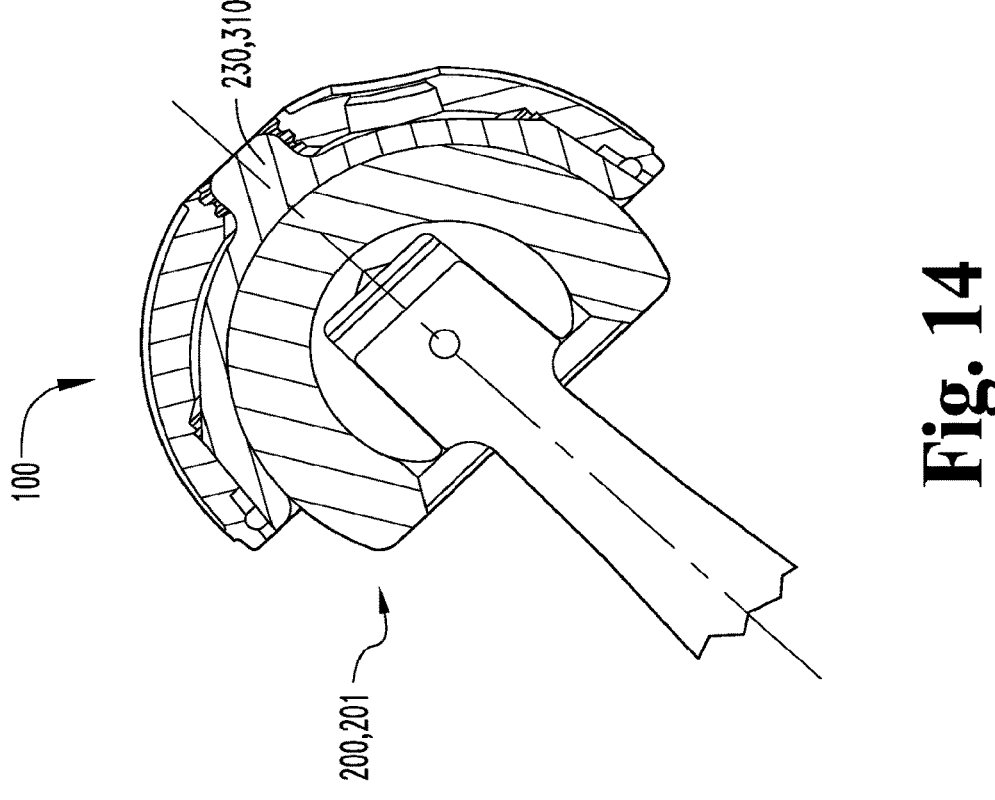
FIGS. 13 and 14 are additional views of the total hip arthroplasty system illustrated in FIG. 1 with the dual-mobility assembly in the first configuration illustrated in FIG. 5.
Figure 13:
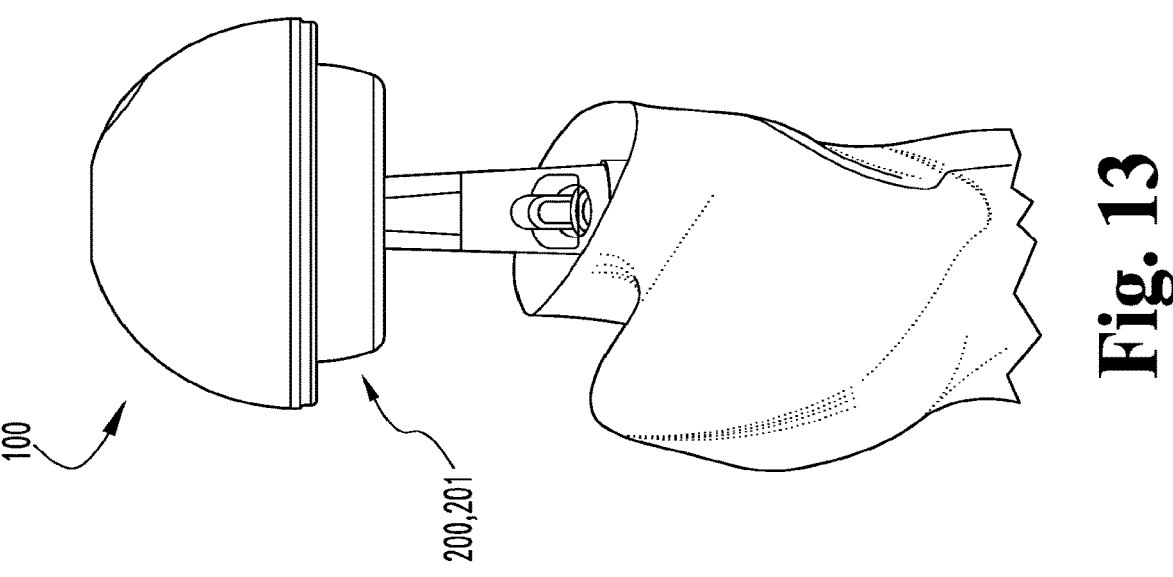

FIGS. 5, 13, and 14 illustrate the system 100 with the dual-mobility assembly 200 in a first configuration 201, in which the liner 230 is of the first liner species 310. In the illustrated form, the first effective height 342 is substantially equal to the depth dimension 133 of the cup cavity 123, and the liner cavity height 343 is substantially equal to half the diameter 268 of the second sphere 260. As a result, the cup end face 121 is aligned with the liner end face 231, and the second pivot point 276 is located on the coplanar end face planes 121', 231'. Additionally, the central axis 127 of the cup 120 is aligned with the geometric axis 237 and the rotational axis 247 of the liner 230, such that the second pivot point 276 is coincident with the reference point 126. Thus, when the dual-mobility assembly 200 is provided in the first configuration 201, both the lateral offset distance and the transverse offset distance of the dual pivot 270 relative to the reference point 126 are zero.

Figure 6:
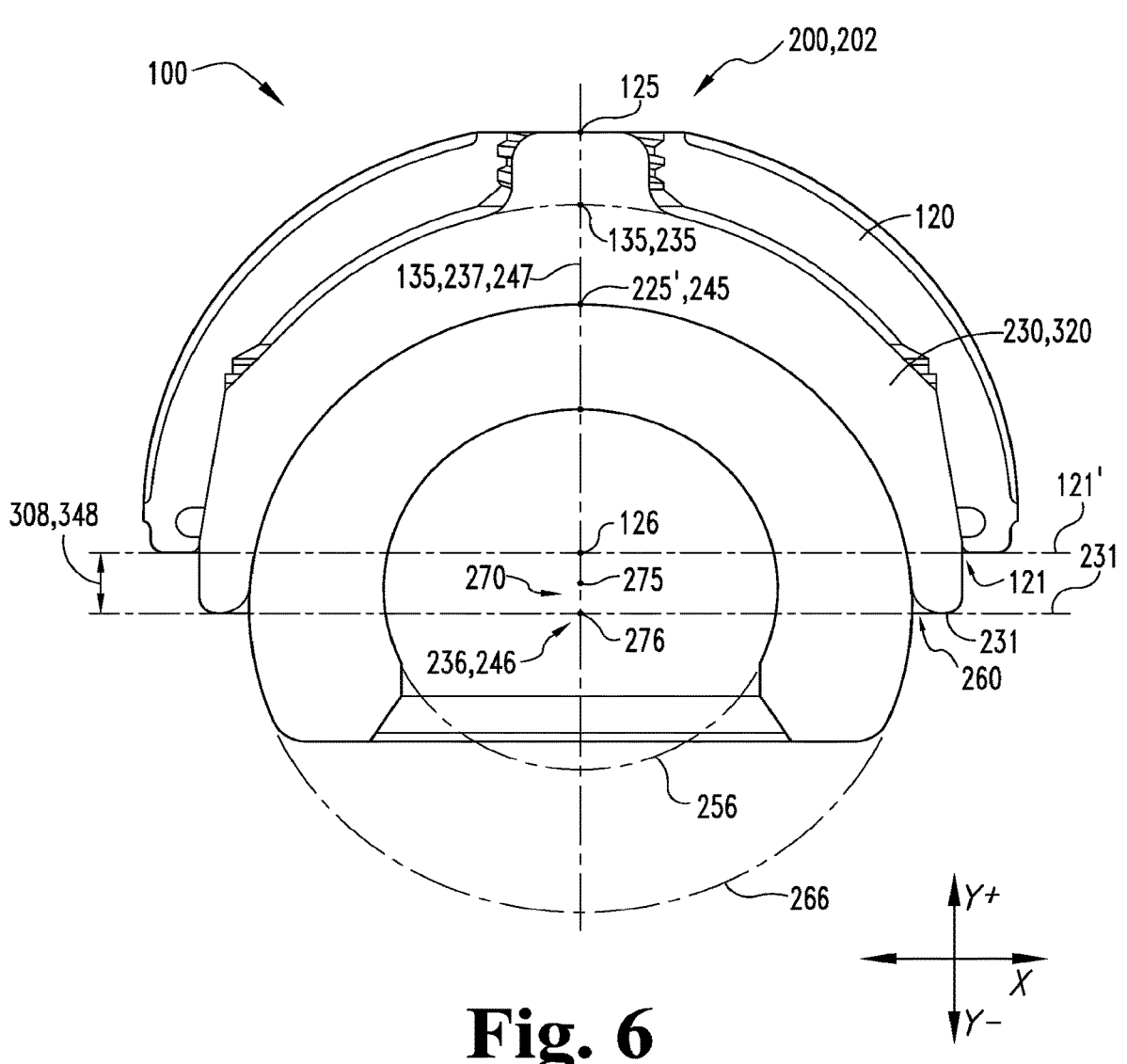
FIG. 6 is a cross-sectional view of a second configuration of the dual-mobility assembly which includes the second liner species illustrated in FIG. 4.
Figure 16:
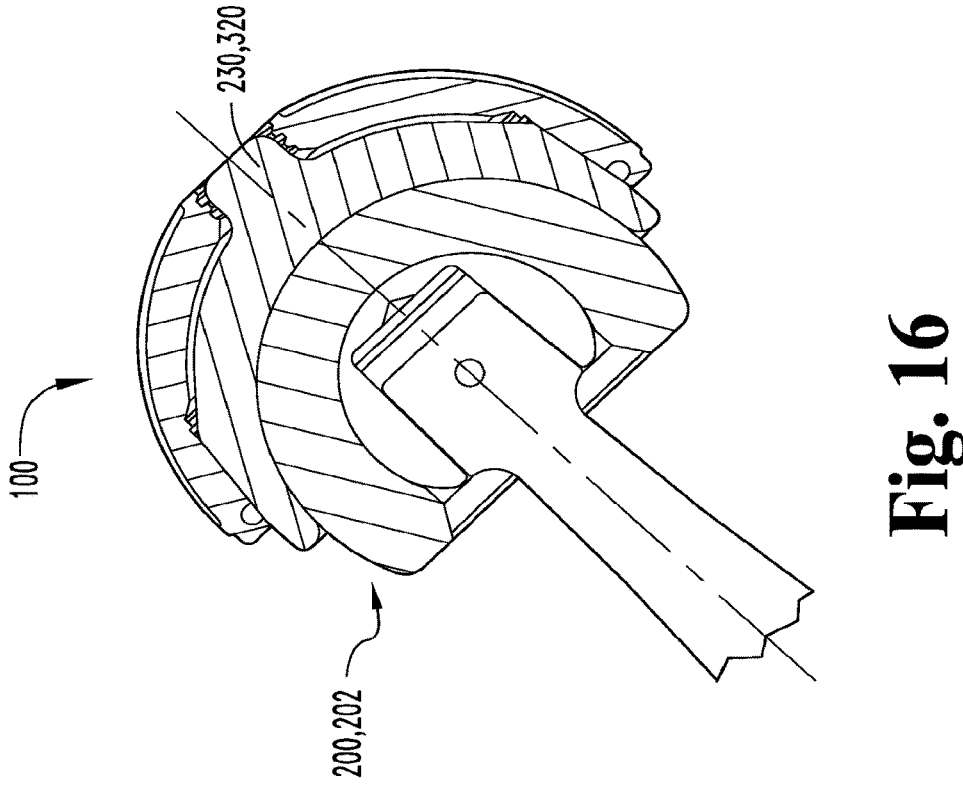
FIGS. 15 and 16 are additional views of the total hip arthroplasty system illustrated in FIG. 1 with the dual-mobility assembly in the second configuration illustrated in FIG. 6.
Figure 15:
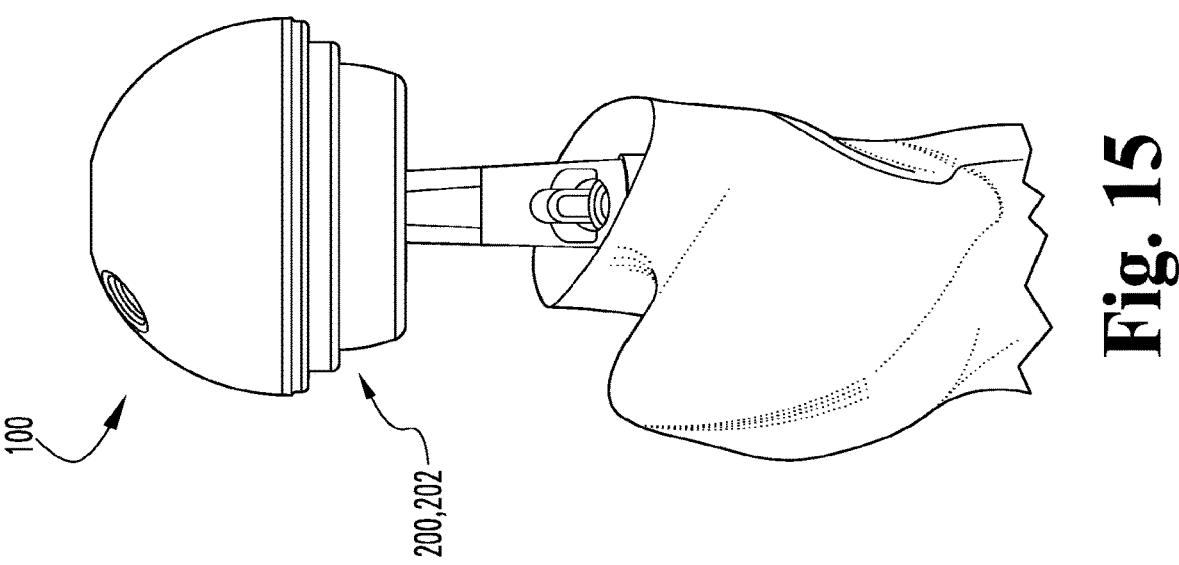

FIGS. 6, 15 and 16 illustrate the system 100 with the dual-mobility assembly 200 in a second configuration 202, in which the liner 230 is of the second liner species 320. In the illustrated embodiment, the second effective height 342' is greater than the depth dimension 133 of the cup cavity 123, and the liner cavity height 343 is substantially equal to half the diameter 268 of the second sphere 260. As a result, the second pivot point 276 is located on the liner end face plane 231', which is offset from the cup end face plane 121' in the lateral direction (downward in FIG. 6). Accordingly, when the dual-mobility assembly 200 is provided in the second configuration 202, the dual pivot 270 has a lateral offset distance 308 defined by the mediolateral distance between the end face planes 121', 231'. Additionally, the central axis 127 of the cup 120 is aligned with the geometric and rotational axes 237, 247 of the liner 230. Thus, when the dual-mobility assembly 200 is provided in the second configuration 202, the transverse offset distance of the dual pivot 270 relative to the reference point 126 is zero.

Figure 7:
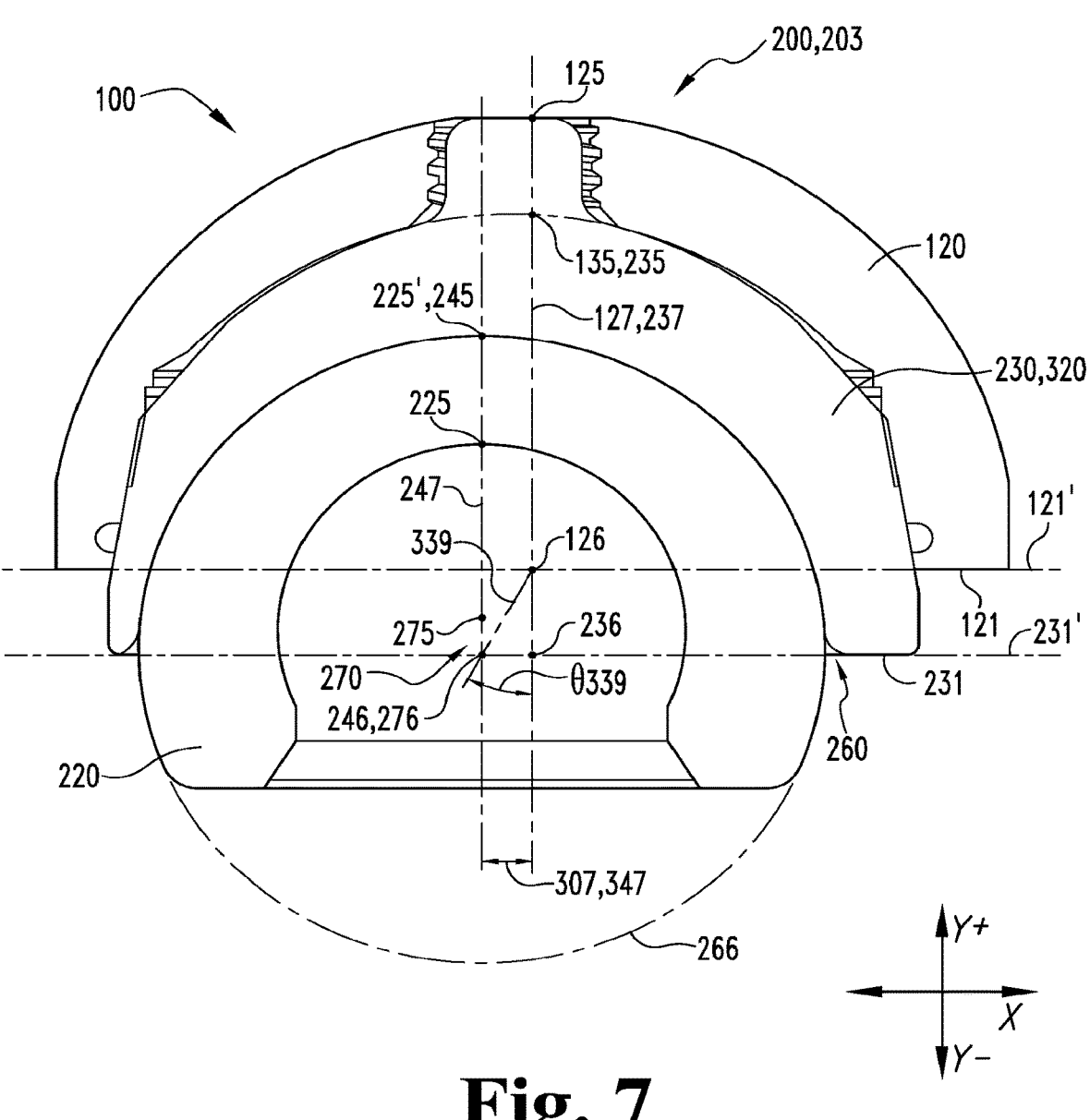
FIG. 7 is a cross-sectional view of a third configuration of the dual-mobility assembly which includes the third liner species illustrated in FIG. 4.
Figures 17, 18:
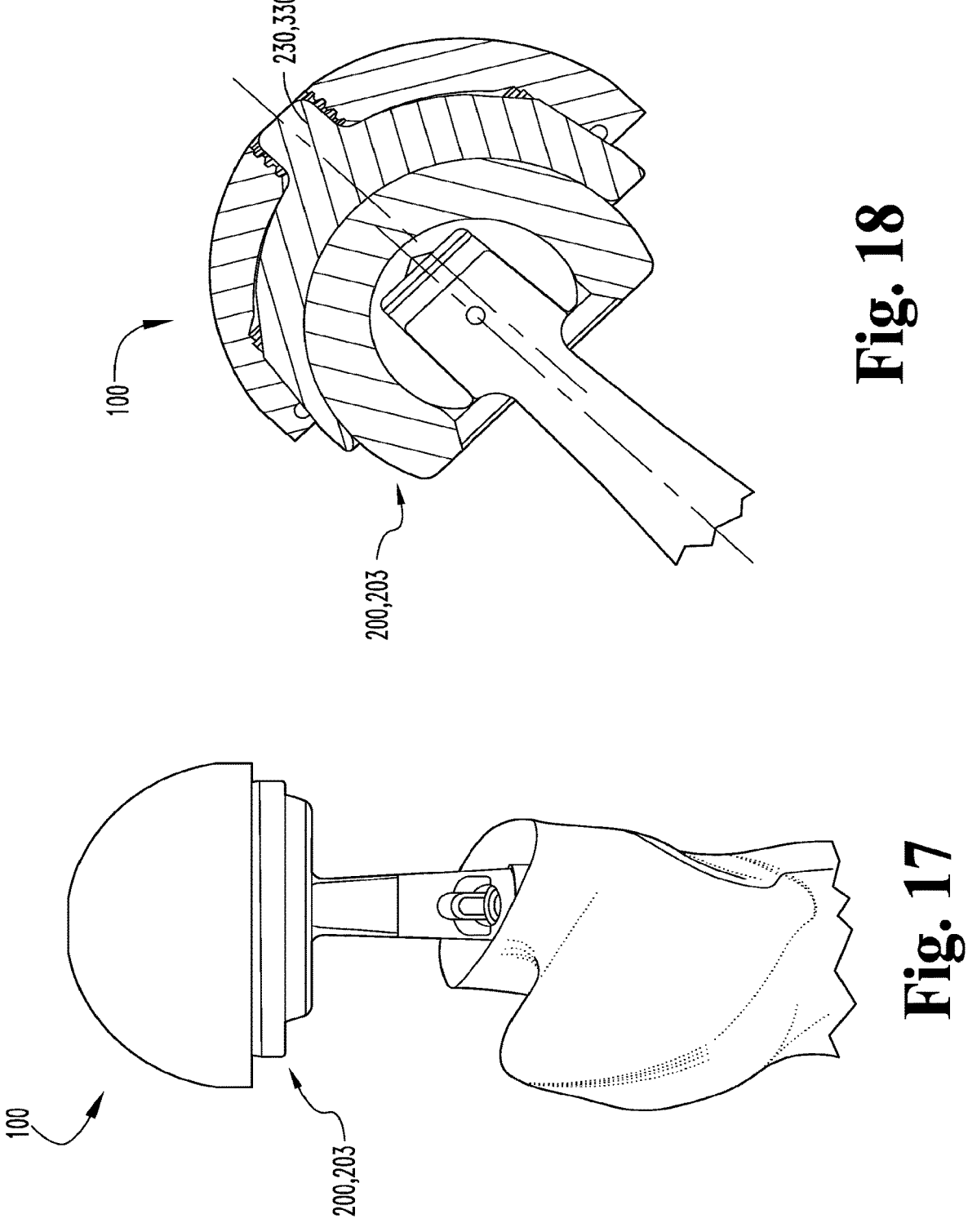
FIGS. 17 and 18 are additional views of the total hip arthroplasty system illustrated in FIG. 1 with the dual-mobility assembly in the third configuration illustrated in FIG. 7.

FIGS. 7, 17 and 18 illustrate the system 100 with the dual-mobility assembly 200 in a third configuration 203, in which the liner 230 is of the third liner species 330. As noted above, the effective height 242 of the third liner species 330 is the second effective height 342', and the cavity height 243 of the third line species 330 is the cavity height 343. In the illustrated embodiment, the second effective height 342' is greater than the depth dimension 133 of the cup cavity 123, and the cavity height 343 is substantially equal to half the diameter 268 of the second sphere 260. As a result, the second pivot point 276 is located on the liner end face plane 231 which is offset from the cup end face plane 121' in the lateral direction (downward in FIG. 7). Thus, when the dual-mobility assembly 200 is provided in the third configuration 203, the dual pivot 270 has a lateral offset dimension 308 corresponding to the mediolateral distance between the end face planes 121', 231' of the cup 120 and liner 230.

With the dual-mobility assembly 200 in the third configuration 203, the rotational axis 247 is transversely offset from geometric axis 237, which is aligned with the central axis 127 of the cup 120. Thus, the dual pivot 270 is transversely offset from the reference point 126 by a non-zero transverse offset dimension 307 corresponding to the transverse distance 347 between the geometric axis 237 and the rotational axis 247. As a result of the transverse offset dimension 307 and the lateral offset dimension 308, a line 339 extending between the reference point 126 and the second pivot point 276 defines an angle .theta.339 relative to the geometric axis 237 and the central axis 127.

While the illustrated liner family 300 includes three liner species 310, 320, 330, it should be understood that a liner family may include more or fewer liner species having additional or alternative configurations. For example, each liner species within a liner family 300 may have a unique combination of values for the transverse and lateral offset distances 347, 348, thereby providing for different configurations of the dual-mobility assembly 200 with different combinations of the transverse offset 307 and lateral offset 308. In certain embodiments, the dual-mobility assembly 200 may be provided as a kit including one or more component families. Each component family may include a plurality of component species having varying characteristics such as, for example, dimensions, materials, and/or finishes. In such forms, the dual-mobility assembly 200 may be assembled in each of a plurality of configurations, each configuration including a unique combination of selected component species.

Figure 8:
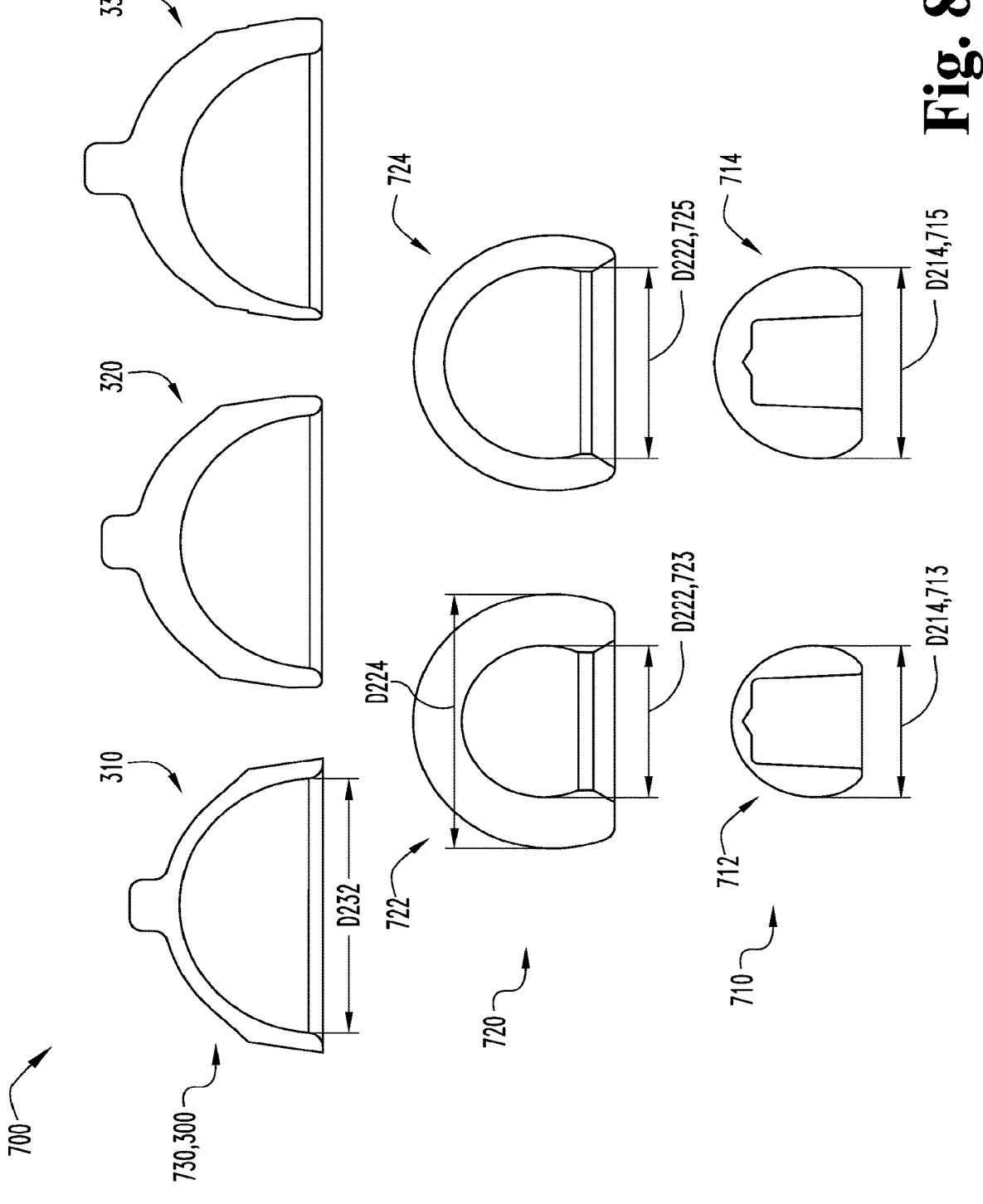
FIG. 8 is a cross-sectional view of a dual-mobility assembly kit according to one embodiment.

With additional reference to FIG. 8, a dual-mobility kit 700 according to certain embodiments includes a head family 710, an insert family 720, and a liner family 730. In the illustrated embodiment, the liner family 730 is provided in the form of the above-described liner family 300. The kit 700 is configured for use with the femoral component 110 and the acetabular cup 120, and may be utilized to form the dual-mobility assembly 200 in each of a plurality of configurations having different characteristics.

The head family 710 includes a plurality of head species 712, 714, each of which is configured for use with the femoral component 110. Accordingly, each of the head species 712, 714 may be utilized as the head 210 for the dual-mobility assembly 200. The head family 710 is configured to provide one or more variable characteristics for the head 210, and each head species 712, 714 has a unique set of values for the one or more variable characteristics. In the illustrated embodiment, the first head species 712 and the second head species 714 have different outer diameters, such that the set of variable characteristics provided by the head family 710 includes the outer diameter for the head 210. For example, the first head species 712 may have an outer diameter 713 of about 22 millimeters (mm), and the second head species 714 may have an outer diameter 715 of about 28 mm. It is also contemplated that the head family 710 may include one or more additional or alternative variable characteristics such as, for example, the material of which the head 210 is formed. By way of example, one head species may be formed of a ceramic material, while another head species may be formed of a metallic material, such as oxidized zirconium, diffusion-hardened oxidized zirconium, or a cobalt-chromium alloy.

The insert family 720 includes a plurality of insert species 722, 724, each of which may be utilized as the insert 220 for the dual-mobility assembly 200. The insert family 720 is configured to provide one or more variable characteristics for the head insert 220, and each insert species 722, 724 has a unique set of values for the one or more variable characteristics. In the illustrated embodiment, the first insert species 722 and the second insert species 724 have different inner diameters, such that the set of variable characteristics provided by the insert family 720 includes the inner diameter of the insert 220. By way of example, the first insert species 722 may have an inner diameter 723 of about 22 mm and be configured for use with the first head species 712.

Similarly, the second insert species 724 may have an inner diameter 725 of about 28 mm and be configured for use with the second head species 714. In the illustrated embodiment, each of the insert species 722, 724 has the same outer diameter. As a result, each of the insert species 722, 724 is configured for use with each of the liner species 310, 320, 330. It is also contemplated that the outer diameter of the insert 220 may be a variable characteristic of the insert family 720. In such forms, the inner diameter of the liner 230 may be a variable characteristic of the liner family 730.

As noted above, the location of the first pivot point 275 within the insert 220 corresponds to the configuration of the inner surface 222, and the location of the second pivot point 276 within the insert 220 corresponds to the configuration of the outer surface 224. In certain embodiments, the relative positions of the first and second pivot points 275, 276 may be a variable characteristic of the insert family 720. For example, a first insert species may have an offset distance 279 of zero, a second insert species may have a first non-trivial onset distance, and a third insert species may have a second non-trivial offset distance greater man the first non-trivial offset distance. Additionally or alternatively, the lateral and/or transverse components of the offset distance may vary from species to species.

In certain embodiments, the kit 700 may be configured for use with an existing femoral component 110 and/or an existing acetabular cup 120. For example, if the patient has previously undergone a partial or total hip arthroplasty procedure in which the femoral component 110 and/or the acetabular cup 120 was implanted, it may be disadvantageous or harmful to remove the implanted component, for example in the event that significant bone ingrowth has occurred. In such a case, the dual-mobility kit 700 may be utilized to build a dual-mobility assembly 200 for a revision procedure. Such a revision procedure may improve the performance of the hip joint without requiring removal of the previously implanted femoral component 110 and/or acetabular cup 120.

In other embodiments, the dual-mobility kit 700 may be provided in a kit for the system 100, for example in the event that the system 100 is to be used in a primary hip arthroplasty procedure. Such a system kit may father include the femoral component 110 and/or the acetabular cup 120, or may include a femoral component family and/or an acetabular cup family from which appropriate species of the component 110 and/or cup 120 may be selected.

With continued reference to FIGS. 5-7, an exemplary use case scenario for the illustrated hip replacement system 100 and dual-mobility assembly kit 700 will now be described. Alter the femoral component 110 and acetabular cup 120 have been implanted, the surgeon selects an initial configuration for the dual-mobility assembly 200 based on patient information and professional judgment. For example, if a first articular interface diameter 258 of 22 mm is desired, the surgeon may initially select a head 210 of the first head species 712, an insert 220 of the second insert species 722, and a liner 230 of the first liner species 310. The head 210 and insert 220 may then be releasably mounted to the femoral component 110 by inserting the head 210 into the insert cavity 223, and inserting the tapered end portion 118 into head cavity 213 such that the tapered walls 119, 219 engage one another. Additionally, the liner 230 may be releasably mounted in the cup 120 by inserting the liner 230 into the cup cavity 123 and engaging the cup inner surface 122 with the liner outer surface 234. The insert 220 may then inserted into the liner cavity 233 to complete the provisional implantation of the system 100 with the dual-mobility assembly 200 in the first configuration 201 (FIGS. 5, 13 and 14).

With provisional implantation of the system 100 completed, the femur may be moved through a normal range of motion to evaluate performance characteristics of the reconstructed hip joint such as, for example, kinematic and/or kinetic performance characteristics. In the event that the performance characteristics are deemed to be unsatisfactory, one or more of the modular components of the dual-mobility assembly 200 may be replaced while the femoral component 110 and acetabular cup 120 remain implanted. The steps of reconfiguring the assembly 200 and evaluating the provisionally implanted system 100 may be repeated as needed until desired performance characteristics are achieved. Once the performance characteristics of the hip joint are deemed to be satisfactory, a final implantation of the system 100 may be performed.

In certain embodiments, each component of the dual-mobility assembly 200 is configured for use as both a trial component and a final component. In such forms, final implantation of the system 100 may include securing the head 210 to the femoral component 110 and securing the liner 230 to the cup 120. Such securing may, for example, involve using fixation devices of a more permanent nature, such as cement, self-locking features, and/or fasteners.

In other embodiments, one or more components of the dual-mobility assembly 200 may be configured as trial components that are replaced with final components after the performance characteristics of the hip joint are deemed to be satisfactory. As one example, the above-described liner family 300 may be a trial liner family, and the kit 700 may further include a final liner family. Each of the trial liner species may be substantially similar to a corresponding one of the final liner species while having one or more characteristics different from those of the corresponding final liner species. For example, the trial liner species may lack certain features that render the corresponding final liner species suitable for final implantation, and/or the trial liner species may include certain features that facilitate the interchanging of trial liners of different species. By way of illustration, the final liners may include self-locking features that engage the cup 120 and inhibit removal of the liner from the cup 120, and the trial liners may lack such self-locking features in order to facilitate removal of the trial liners when reconfiguring the assembly 200. In embodiments in which the assembly 200 includes both a trial component family and a final component family, final implantation of the system 100 may include noting the trial component species that resulted in satisfactory performance characteristics, and replacing the trial component of the noted species with a final component of a corresponding final component species.

In the example use case scenario, the surgeon determines that the first configuration 201 of the dual-mobility assembly 200 results in unsatisfactory or suboptimal performance characteristics for the system 100. More specifically, the surgeon determines that a lateral offset corresponding to the lateral offset distance 308 is desired for the dual pivot 270, and accordingly replaces the initially-selected liner of the first species 310 with a liner of the second species 320. Criteria that may indicate that a lateral offset is desirable may, for example, include insufficient tension in the ligaments and/or other soft tissue. Such insufficient soft tissue tension may be the result of deterioration of soft tissue and/or bony tissue in the vicinity of the hip joint, the acetabular socket having been reamed to a greater depth than indicated in the surgical plan, or other anatomical and/or surgical conditions.

After replacing the liner of the first species 310 with the liner of the second species 320, the system 100 is provisionally implanted with the dual-mobility assembly 200 in the second configuration 202 (FIGS. 6, 15 and 16). After evaluating the performance characteristics of the hip joint, the surgeon may determine that a transverse offset dimension 307 is desired in addition to the lateral offset dimension 308, for example, in the event that additional soft tissue tension is desired. In such a case, the surgeon may select a liner of the third species 330 to replace the previously-selected liner of the second species 320. The surgeon may then estimate an optimal orientation for the transverse offset 307 relative to the anatomy of the patient, and insert the liner 230 into the cup 120 in a corresponding rotational orientation. The system 100 is then reassembled with the dual-mobility assembly 200 in the third configuration 203 (FIGS. 7, 17 and 18), and performance of the hip joint is re-evaluated.

Should the surgeon determine that a different orientation for the transverse offset dimension 307 may result in improved performance characteristics, the liner 230 may be removed from the cup 120 and reinserted in a new rotational orientation. In other words, the dual pivot 270 may be revolved about the central axis 127 of the cup 120 by removing the liner 230 from the cup 120, rotating the liner 230 about the geometric axis 237, and reinserting the liner 230 in the new rotational position.

Figure 9:
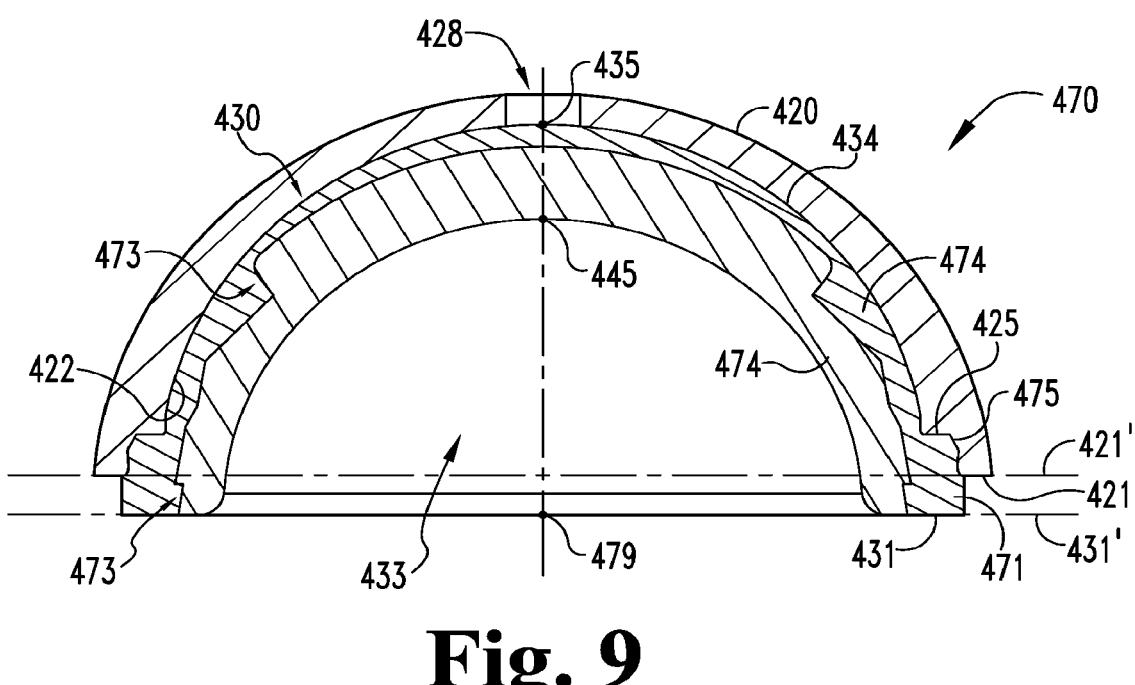
FIG. 9 is a cross-sectional view of a liner according to one embodiment.
Figure 10:
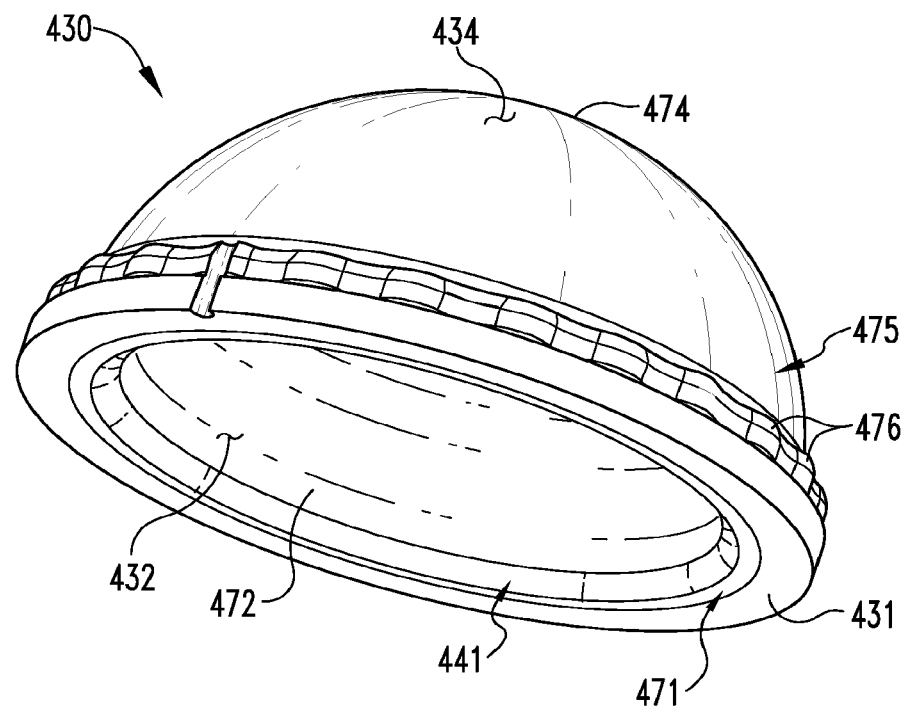
FIG. 10 is a perspective view of the liner illustrated in FIG. 9.
Figure 19:
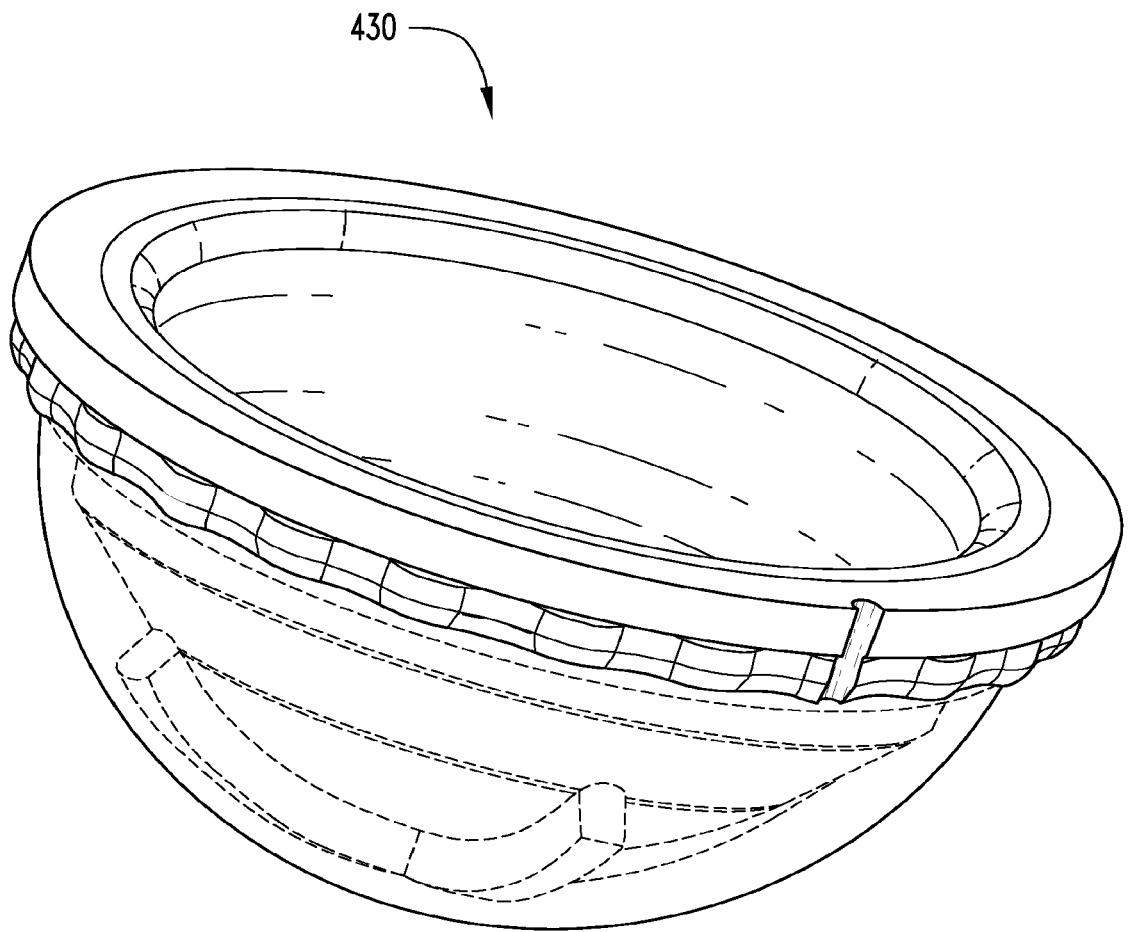
FIG. 19 is an additional illustration of the liner illustrated in FIGS. 9 and 10.

As noted above, the dual-mobility assembly 200 may be provided as a kit 700 configured for use with an existing femoral component 110 and/or an existing acetabular cup 120. FIGS. 9, 10 and 19 illustrate an example of a liner 430 that may be included in such a kit. The liner 430 is substantially similar to the liner 230 described above, and similar reference characters are used to indicate similar elements and features. The liner 430 also includes certain elements and features 470 that are not necessarily included in the liner 230 and/or were not specifically described above. In the interest of conciseness, the following description of the liner 430 focuses primarily on these elements and features 470.

The liner 430 includes an inner layer 472 defining the inner articular surface 432, and an outer layer 474 defining the outer surface 434. The inner layer 472 is formed of a first material, and the outer layer 474 is formed of a second material. While other materials are contemplated, in the illustrated form, the inner layer 472 is formed of a metal, and the outer layer 474 is formed of a polymer such as, for example, cross-linked polyethylene. The inner and outer layers 472, 474 include mating features 473 that aid in securing the layers 472, 474 to one another. In certain embodiments, the liner 430 may be formed by molding the outer layer 474 onto the inner layer 472. In other embodiment, the layers 472, 474 may be formed separately, and the inner layer 472 may be press-lit into the outer layer 474.

The liner 430 is configured for use with an existing acetabular cup 420, which may have been implanted to the patient in a previous surgical procedure. The liner 430 includes a rim 471 defining the liner end face 431, and a locking ring 475 termed "above" (i.e., medially of) the rim 471. The locking ring 475 is configured to engage a corresponding locking ring 425 formed in the cup 420 adjacent the end face 421 thereof. More specifically, each of the locking rings 425, 475 includes a series of recesses and protrusions which engage with one another to at least partially secure the liner 430 to the cup 420. When the liner 430 is inserted into the cup 420 and the locking rings 425, 475 are engaged with one another, the rim 471 extends laterally beyond the cup end face 421 such that the liner end face plane 431' is positioned "below" (i.e., laterally of) the cup end face plane 421'. As a result, the liner 430 is capable of providing a pivot point 479 having a positive mediolateral offset corresponding to the lateral offset 308 provided by the second and third liner species 320, 330.

In certain embodiments, the dual-mobility assembly 200 may be provided as a revision kit configured for use with the cup 420, for example if the cup 420 was previously implanted in the patient. Such a revision kit may include a liner family including a plurality of liner species similar to the liner 430. Like the second liner species 320, the liner 430 is configured to provide a lateral offset without providing a transverse offset. Those having skill in the art will readily appreciate that the dimensions of the liner 430 may be modified to generate additional liner species corresponding to the first and third liner species 310, 330 described above.

Figure 11:
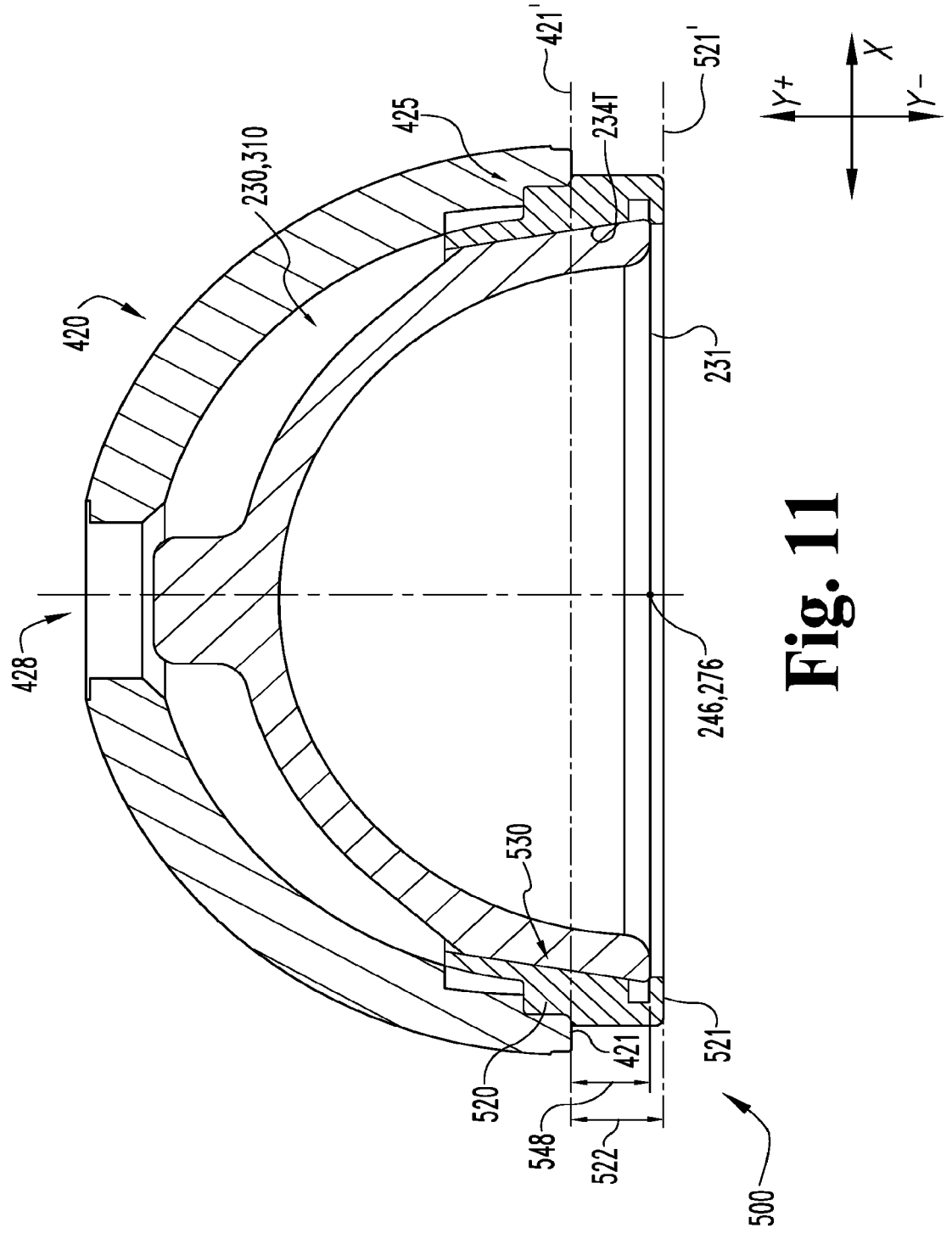
FIG. 11 is a cross-sectional view of an acetabular cup assembly according to one embodiment.

FIG. 11 illustrates an adapter ring 500 according to certain embodiments. The adapter ring 500 is configured for use with the cup 420 and the liner 230 of the first species 310. More specifically, the adapter ring 500 is configured to provide the first liner species 310 with a lateral offset 548 corresponding to the lateral offset 348 provided by the second liner species 320. The adapter ring 500 includes a locking ring 510, a rim 520 positioned laterally of the locking ring 510, and a tapered inner surface 530. The locking ring 510 is configured to engage the locking ring 425 of the cup 420 in a manner similar to the locking ring 475 of the liner 430. The rim 520 has a mediolateral width 522, which is dimensioned such that the end face plane 521' of the adapter ring 500 is laterally offset from the end face plane 421' of the cup 420.

The tapered inner surface 530 is configured to engage the tapered outer surface 234T to prevent the liner 230 from being fully seated in the cup 420. As a result, the end face 231 of the liner 230 is offset from the end face 421 of the cup 420 in the lateral direction. Thus, the adapter ring 500 enables the first liner species 310 to be used with the legacy cup 420 while providing a lateral offset 548 for the second pivot point 276. The lateral offset distance 548 provided by an adapter ring may be adjusted by selecting an adapter ring species having a greater or lesser mediolateral width 522. Additionally or alternatively, the lateral offset dimension 548 may be adjusted by selecting an adapter ring species in which the tapered inner surface 530 has the same taper angle, but a greater or lesser diameter at the end face thereof.

Figure 12:
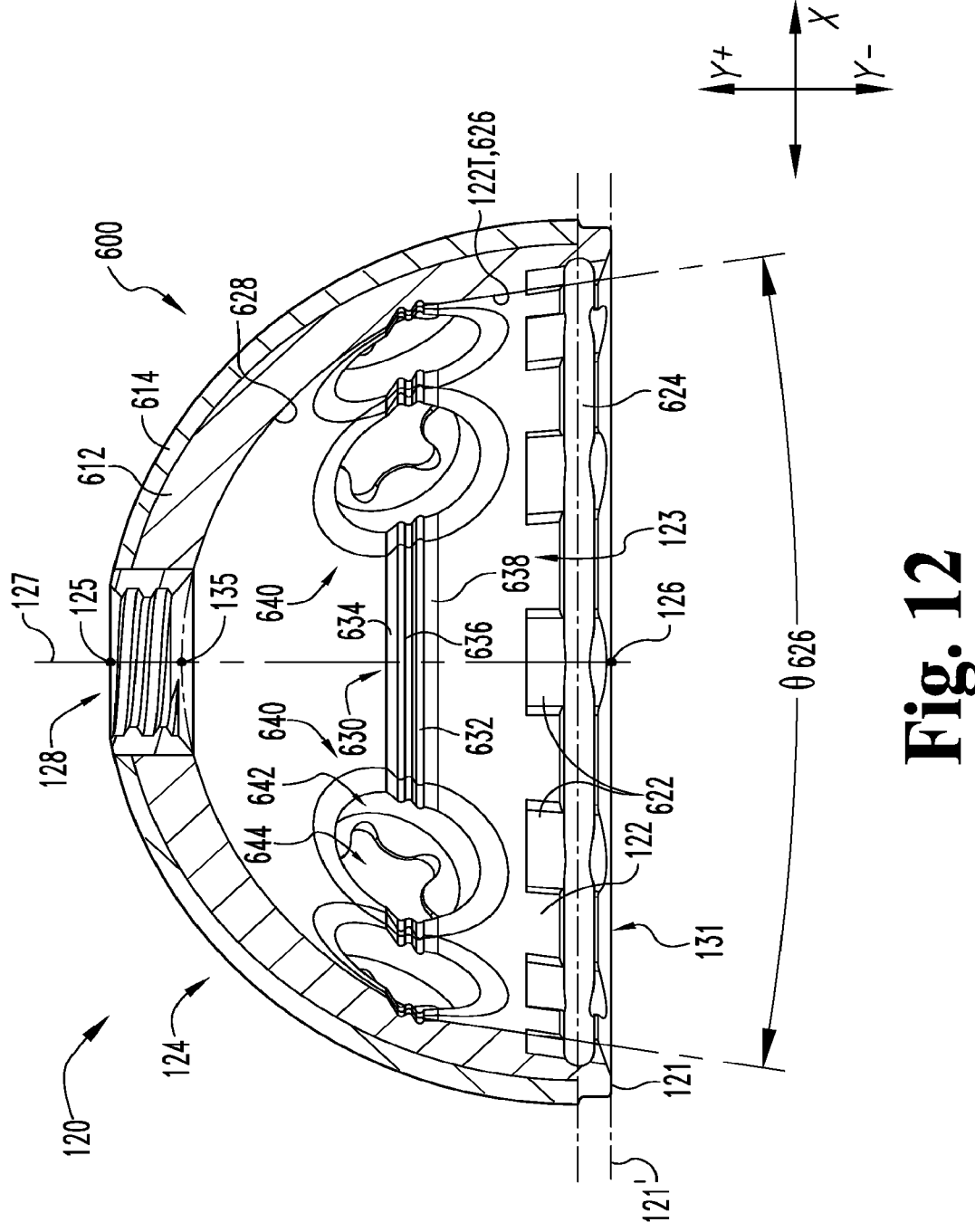
FIG. 12 is a cross-sectional illustration of an acetabular cup which may be utilized in connection with certain embodiments of the invention.

FIG. 12 is a cross-sectional illustration of the above-described acetabular cup 120, and illustrates various features 600 of the cup 120 that were not specifically described above. In the interest of conciseness, the following descriptions of the cup 120 locus primarily on these elements and features 600. The cup 120 includes an inner layer 612 defining the inner surface 122, and an outer layer 614 defining the outer surface 124. The inner layer 612 may be provided as a substantially solid layer, and the outer layer 614 may be porous to encourage bone ingrowth. In certain embodiments, the inner layer 612 may be polished to provide the inner surface 122 with a substantially smooth finish.

The inner surface 122 includes a plurality of outwardly-extending scallops 622, a tapered wall 626 positioned "above" (i.e., medially of) the end face 121, a curved wall 628 positioned medially of the tapered wall 626, and a locking feature 630 located between the tapered wall 626 and the cursed wall 628. The tapered wall 626 has a geometry corresponding to that of the tapered wall 122T such that the tapered walls 122T, 626 are capable of flushly engaging one another. The scallops 622 are formed adjacent the end face 121, and are connected to the end face opening 131. The inner surface 122 also includes an annular channel 624, which is medially offset from the end face 121 and intersects the scallops 622. The tapered wall 626 is symmetrical about the central axis 127, and defines a predetermined taper angle .theta.626. In the illustrated form, the predetermined taper angle .theta.626 is about 18.degree. such that the tapered wall 626 defines an angle of about 9.degree. relative to the central axis 127. In the illustrated form, the curved wall 628 is a spherical cap, such as a cap of a sphere that is centered at the reference point 126, and has a radius corresponding to the cavity depth 133.

The locking feature 630 includes a lateral or lower groove 632, a medial or upper groove 634, and a protrusion 636 located between the grooves 632, 634. The locking feature 630 may further include a wall 638 that extends between the tapered wall 626 and the lower groove 632, and which may be arranged parallel to the central axis 127. As noted above, the liner 230 may be provided as either a final liner or a trial liner. A final liner may include a corresponding locking feature configured to engage the locking feature 630 such that the engaged locking features form a self-locking mechanism that inhibits removal of the final liner from the cup 120. By way of example, such a corresponding locking feature may include a lower bump configured to be received in the lower groove 632, an upper bump configured to be received in the upper groove 634, and a recess configured to receive the protrusion 636. In contrast, one or more features of the corresponding locking feature may be omitted from the trial liner, such that the trial liner is more easily removed from the cup 120.

The cup 120 may further include one or more fixation features 640 to facilitate fixation of the cup 120 to the hip within the prepared acetabular socket. In the illustrated form, each fixation feature 640 includes counter-sink 642 that is recessed relative to the inner surface 132, and a star-shaped opening 644 that is formed within the counter-sink 642. After the cup 120 is initially implanted in the acetabular socket, the fixation features 640 may cooperate with fasteners to secure the cup 120 within the socket. For example, the shank of the fastener may extend through the opening 644 and engage the hip bone, and the head of the fastener may be received in the counter-sink 642 to prevent the fastener from impinging on the liner 230.

An embodiment of the present application relates to a system including a cup configured for implantation in an acetabular socket, and a dual-mobility assembly defining a dual pivot including a first pivot point and a second pivot point. The cup has a geometric axis defining a medial direction and an opposite lateral direction, and comprises: a cup face extending along a cup face plane and defining a cup opening; a cup apex positioned medially of the cup face, wherein the geometric axis extends through the cup apex and intersects the cup face plane at a reference point; and a cup inner surface defining a cup cavity connected with the cup opening, wherein the cup inner surface includes a tapered wall centered about the geometric axis, wherein the tapered wall tapers radially inwardly in the medial direction. The dual-mobility the dual-mobility assembly comprises: a liner sealed in the cup cavity, the liner including a liner outer surface and a liner inner surface, wherein the liner outer surface includes a tapered portion that is engaged with the tapered wall of the cup and is centered about the geometric axis, and wherein the liner inner surface defines a liner cavity and is spherical about the second pivot point; an insert seated in the liner cavity, the insert including an insert outer surface and an insert inner surface, wherein the insert outer surface is spherical about the second pivot point, and wherein the insert inner surface defines an insert cavity and is spherical about the first pivot point; and a head seated in the insert cavity, the head including a head outer surface and a head inner surface, wherein the head outer surface is spherical about the first pivot point, and wherein the head inner surface defines a head cavity sized and configured to receive a portion of a femoral component. The dual-mobility assembly is adjustable between a plurality of configurations, including a first configuration and a second configuration. With the dual-mobility assembly in the first configuration, the liner is of a first liner species, and the second pivot point has a first position relative to the reference point. With the dual-mobility assembly in the second configuration, the liner is of a second liner species, and the second pivot point has a second position relative to the reference point. The first position is different from the second position, and at least one of the first position or the second position is offset from the reference point in the lateral direction.

In certain forms, at least one of the first position or the second position is offset from the geometric axis in a direction transverse to the geometric axis.

In certain forms, each of the first position and the second position is offset from the reference point in the lateral direction.

In certain forms, the first position is located on the geometric axis, and wherein the second position is offset from the geometric axis in a direction transverse to the geometric axis.

In certain forms, the first position is coincident with the reference point, and wherein the second position is offset from the reference point in the lateral direction.

In certain forms, the liner inner surface and the insert outer surface define an outer articular interface having an outer articular interface diameter, wherein the insert inner surface and the head outer surface define an inner articular interface having an inner articular interface diameter. In a refinement, with the dual-mobility assembly in the first configuration, the insert is of a first insert species, the outer articular interface diameter has an outer articular interface diameter first value, and the inner articular interface has an inner articular interface diameter first value; wherein, with the dual-mobility assembly in the second configuration, the insert is of a second insert species, the outer articular interface diameter has an outer articular interface diameter second value, and the inner articular interface has an inner articular interface diameter second value: and wherein at least one of (i) the outer articular interface diameter first value is different from the outer articular interface diameter second value; or (ii) the inner articular interface diameter first value is different from the inner articular interface diameter second value.

In certain forms, the first configuration is a first trial configuration and the second configuration is a second trial configuration; wherein the first liner species is a first trial liner species and the second liner species is a second trial liner species; wherein the plurality of configurations further includes a first final configuration in which the liner is of a first final liner species and the second pivot point has the first position relative to the reference point, and a second final configuration in which the liner is of a second final liner species and the second pivot point has the second position relative to the reference point; wherein each of the trial liner species includes a first set of features that facilitates adjustment of the dual-mobility assembly between the first trial configuration and the second trial configuration; and wherein each of the final liner species includes a second set of features that facilitates fixation of the dual-mobility assembly in the first final configuration and the second final configuration.

Another embodiment of the present application relates to a system including a cup, a femoral component and a dual-mobility assembly. The cup is configured for implantation in an acetabular socket, the cup comprising a cup outer surface and a cup inner surface defining a cup cavity, the cup has a hemispherical geometry basing a cup center point a cup apex offset from the cup center point in a medial direction, and a geometric axis extending through the cup center point and the cup apex, and the geometric axis defines the medial direction a lateral direction opposite the medial direction. The femoral component is configured for implantation in a femur. The dual-mobility assembly includes a first articular interface centered about a first pivot point a second articular interface centered about a second pivot point, and a dual pivot including the first pivot point and the second pivot point wherein at least one of the first pivot point or the second pivot point is offset from the cup center point in the lateral direction such that the dual pivot is located at least partially outside the cup cavity, wherein the dual-mobility assembly is mounted between the cup and the femoral component such that the cup and the femoral component are pivotable relative one another about the dual pivot the dual-mobility assembly comprises: a head mounted to the femoral component, the head comprising a head inner surface and a head outer surface, wherein the head inner surface is engaged with the femoral component, and wherein the head outer surface is centered about the first pivot point and partially defines the first articular interface; a liner seated in the cup cavity, the liner including a liner outer surface and a liner inner surface, wherein the liner outer surface is engaged with the cup inner surface, and wherein the liner inner surface is centered about the second pivot point and partially defines the second articular interface; and an insert seated between the head and the liner, the insert comprising an insert inner surface and an insert outer surface, wherein the insert inner surface is centered about the first pivot point and further defines the first articular interface, and wherein the insert outer surface is centered about the second pivot point and further defines the second articular interface.

In certain forms, the second pivot point is offset from the cup center point in the lateral direction.

In certain forms, the second pivot point is offset from the cup center point in the lateral direction, and the first pivot point is offset from the cup center point in the lateral direction.

In certain forms, the second pivot point is offset from the cup center point in the lateral direction, the first pivot point is offset from the cup center point in the lateral direction, and the first pivot point is offset from the second pivot point in the medial direction.

In certain forms, the second pivot point is offset from the cup center point in the lateral direction, the first pivot point is offset from the cup center point in the lateral direction, and the second pivot point is offset from the cup center point in a direction transverse to the geometric axis.

Another embodiment of the present application relates to a system comprising a cup and a plurality of liners. The cup is configured for implantation in an acetabular socket, the cup has a cup geometric axis defining a medial direction and an opposite lateral direction, and the cup comprises: a cup face extending along a cup face plane and defining a cup opening: a cup apex positioned medially of the cup face, wherein the cup geometric axis extends through the cup apex and intersects the cup face plane at a reference point; and a cup inner surface defining a cup cavity connected with the cup opening, wherein the cup inner surface includes a tapered wall centered about the cup geometric axis, wherein the tapered wall tapers radially inward in the medial direction. Each of the plurality of liners is configured to be seated in the cup cavity, and each liner comprises: a finer geometric axis, wherein the liner geometric axis is aligned with the cup geometric axis when the liner is seated in the cup cavity; a liner outer surface including a tapered portion configured to engage the tapered wall, wherein the tapered portion is centered about the liner geometric axis; a liner inner surface centered about a first pivot point and having a liner inner diameter, the liner inner surface defining a liner cavity; a transverse offset dimension defined between the first pivot point and the liner geometric axis; and an effective height, wherein with the liner seated in the cup cavity, the first pivot point is offset in the lateral direction from the cup apex by the effective height. A first liner of the plurality of liners has a first transverse offset dimension and a first effective height, wherein with the first liner seated in the cup cavity, the first pivot point has a first position relative to the reference point. A second liner of the plurality of liners has a second effective height greater than the first effective height, wherein with the second liner seated in the cup cavity, the first pivot point has a second position relative to the reference point, and wherein the third position is offset from the reference point in the lateral direction. A third liner of the plurality of liners has a second transverse offset dimension greater than the first transverse offset dimension, wherein with the third liner seated in the cup cavity, the first pivot point has a third position relative to the reference point, and wherein the third position is not located on the cup geometric axis.

In certain forms, the first transverse offset dimension is zero such that the first position is located on the cup geometric axis.

In certain forms, the second liner has the first transverse offset dimension, and wherein the third liner has the second effective height.

In certain forms, the system further comprises a plurality of inserts: wherein each insert comprises an insert outer surface having a spherical geometry that is centered about be first pivot point when the insert is seated in life liner cavity, and an insert inner surface centered about a second pivot point and having an insert inner diameter; wherein a first of the inserts has a first insert inner diameter, and a second of the inserts has a second insert inner diameter greater than the first insert inner diameter. In a refinement, the system further comprises a plurality of heads; wherein each head comprises a head inner surface defining a head cavity sized and shaped to receive a portion of a femoral component, and a head outer surface having a head outer diameter; wherein a first of the heads has a first head outer diameter corresponding to the first insert inner diameter, and wherein a second of the heads has a second head outer diameter corresponding to the second insert inner diameter.

A further embodiment of the present application relates to a system comprising a cup configured for implantation in an acetabular socket, and a dual-mobility assembly defining a dual pivot including a first pivot point and a second pivot point. The cup has a geometric axis defining a medial direction and an opposite lateral direction, and the cup comprises: a cup face extending along a cup face plane and defining a cup opening; a cup apex positioned medially of the cup face, wherein the geometric axis extends through the cup apex and intersects the cup face plane at a reference point; and a cup inner surface defining a cup cavity connected with the cup opening, wherein the cup inner surface includes a tapered wall centered about the geometric axis, wherein the tapered wall tapers radially inwardly in the medial direction. The dual-mobility assembly comprises: a liner seated in the cup cavity, the liner including a liner outer surface and a liner inner surface, wherein the liner outer surface includes a tapered portion that is engaged with the tapered wall of the cup and is centered about the geometric axis, and wherein the liner inner surface defines a liner cavity and is spherical about the second pivot point; an insert seated in the liner cavity, the insert including an insert outer surface and an insert inner surface, wherein the insert outer surface is spherical about the second pivot point, and wherein the insert inner surface defines an insert cavity and is spherical about the first pivot point: and a head seated in the insert cavity, the head including a head outer surface and a head inner surface, wherein the head outer surface is spherical about the first pivot point and wherein the head inner surface defines a head cavity sized and configured to receive a portion of a femoral component. The dual-mobility assembly is adjustable between a plurality of configurations, the plurality of configurations including a first configuration and a second configuration. With the dual-mobility assembly in the first configuration, the liner is of a first liner species, and the second pivot point has a first position relative to the reference point. With the dual-mobility assembly in the second configuration, the liner is of a second liner species, and the second pivot point has a second position relative to the reference point. The first position is different from the second position, and at least one of the first position or the second position is offset from the reference point in the lateral direction.

In certain forms, the cup has a hemispherical geometry centered at the reference point.

In certain forms, at least one of the first position or the second position is offset from the geometric axis in a direction transverse to the geometric axis.

In certain forms, each of the first position and the second position is offset from the reference point in the lateral direction.

In certain forms, the first position is located on the geometric axis, and the second position is offset from the geometric axis in a direction transverse to the geometric axis.

In certain forms, the first position is coincident with the reference point, and wherein the second position is offset from the reference point in the lateral direction.

In certain forms, with the dual-mobility assembly in the first configuration, the first pivot point is offset from the reference point in the lateral direction, and the second pivot point is offset from the first pivot point in the lateral direction.

In certain forms, with the dual-mobility assembly in the first configuration, the first pivot point is offset from the geometric axis in a direction transverse to the geometric axis.

In certain forms, with the dual-mobility assembly in the first configuration, the first pivot point is offset from the reference point in the medial direction.

In certain forms, the liner inner surface and the insert outer surface define an outer articular interface having an outer articular interface diameter, and the insert inner surface and the head outer surface define an inner articular interface having an inner articular interface diameter.

In certain forms, with the dual-mobility assembly in the first configuration, the insert is of a first insert species, the outer articular interface diameter has an outer articular interface diameter first value, and the inner articular interface has an inner articular interface diameter first value; wherein, with the dual-mobility assembly in the second configuration, the insert is of a second insert species, the outer articular interface diameter has an outer articular interface diameter second value, and the inner articular interface has an inner articular interface diameter second value; and wherein at least one of (i) the outer articular interface diameter first value is different from the outer articular interface diameter second value; or (ii) the inner articular interface diameter first value is different from the inner articular interface diameter second value.

In certain forms, the inner articular interface diameter first value is different from the inner articular interface diameter second value; wherein with the dual-mobility assembly in the first configuration, the head is of a first head species, and each of the insert inner surface and the head outer surface has a diameter corresponding to the inner articular interface diameter first value; and wherein with the dual-mobility assembly in the second configuration, the head is of a second head species, and each of the insert inner surface and the head outer surface has a diameter corresponding to the inner articular interface diameter second value.

In certain forms, the first configuration is a first trial configuration and the second configuration is a second trial configuration; wherein the first liner species is a first trial liner species and the second liner species is a second trial liner species; wherein the plurality of configurations further includes a first final configuration in which the liner is of a first final liner species and the second pivot point has the first position relative to the reference point, and a second final configuration in which the liner is of a second final liner species and the second pivot point has the second position relative to the reference point; wherein each of the trial liner species includes a first set of features that facilitates adjustment of the dual-mobility assembly between the first trial configuration and the second trial configuration; and wherein each of the final liner species includes a second set of features that facilitates fixation of the dual-mobility assembly in the first final configuration and the second final configuration.

In certain forms, the system further comprises a femoral component including a body and a neck extending at an angle relative to the body, wherein an end portion of the neck is received in the head cavity such that the cup and the femoral component are pivotable relative to one another about the dual pivot.

In certain forms, the cup inner surface includes a circumferential groove positioned medially of the tapered wall; wherein the liner outer surface includes a circumferential ridge positioned medially of the tapered portion; and wherein the groove and the ridge are engaged with one another and resist relative movement of the cup and the liner along the geometric axis.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:

1. A total hip arthroplasty system comprising:

an acetabular cup configured for implantation in an acetabular socket of a patient, the acetabular cup including an end face, an apex, a cup opening defining a cavity having an inner surface, and a geometric axis defining a medial direction and an opposite lateral direction, the geometric axis extending through the apex and intersects a plane of the end face at a reference point;

a dual-mobility assembly comprising:

a generally hemispherical liner configured for positioning within the cavity of the acetabular cup, the liner comprising a liner cavity, which defines a liner inner surface, and a locking ring formed on a liner outer surface configured to engage a corresponding locking ring formed in the acetabular cup to at least partially secure the liner to the acetabular cup;

an insert configured for positioning within the liner cavity, the insert comprising an insert cavity, which defines an insert inner surface; and a head configured for positioning within the insert cavity, the head comprising a head cavity, which defines a head inner surface; and a femoral component comprising a body and a neck, wherein the neck is configured for at least partial insertion within the head cavity;

wherein the insert is pivotable, relative to the head, about a first pivot point;

wherein the liner is pivotable, relative to the insert, about a second pivot point;

wherein the first and second pivot points are spaced apart from each other and define a dual pivot for the dual-mobility assembly;

wherein, when the femoral component is attached to dual-mobility assembly and the dual-mobility assembly is attached to the acetabular cup, the acetabular cup and the femoral component are pivotable relative to each other about the dual pivot;

wherein the dual-mobility assembly is adjustable between a plurality of configurations, the plurality of configurations including a first configuration and a second configuration;

wherein, with the dual-mobility assembly in the first configuration, the liner is of a first liner species, and the second pivot point has a first position relative to the reference point;

wherein, with the dual-mobility assembly in the second configuration, the liner is of a second liner species, and the second pivot point has a second position relative to the reference point;

wherein the first position is different from the second position, and at least one of the first position or the second position is offset from the reference point in the lateral direction;

wherein the offset has a non-zero value.

2. The total hip arthroplasty system of claim 1, comprising a head family that comprises a plurality of head species that can each be used as the head of the dual-mobility assembly;

wherein the head family is configured to provide one or more variable characteristics for the head, each head species of the plurality of head species having a unique set of values for the one or more variable characteristics for the head.

3. The total hip arthroplasty system of claim 1, comprising an insert family that comprises a plurality of insert species that can each be used as the insert of the dual-mobility assembly;

wherein the insert family is configured to provide one or more variable characteristics for the insert, each insert species of the plurality of insert species having a unique set of values for the one or more variable characteristics for the insert.

4. The total hip arthroplasty system of claim 1, wherein the head comprises a metallic material.

5. The total hip arthroplasty system of claim 4, wherein the metallic material is oxidized zirconium, diffusion-hardened oxidized zirconium, or a cobalt-chromium alloy.

6. The total hip arthroplasty system of claim 5, wherein the liner comprises a metallic material.

7. The total hip arthroplasty system of claim 6, wherein the metallic material from which the liner is formed is oxidized zirconium, diffusion-hardened oxidized zirconium, or a cobalt-chromium alloy.

8. The total hip arthroplasty system of claim 1, wherein the liner comprises a metallic material.

9. The total hip arthroplasty system of claim 8, wherein the metallic material is oxidized zirconium, diffusion-hardened oxidized zirconium, or a cobalt-chromium alloy.

* * * * *